United States Patent
Miller et al.

(10) Patent No.: US 11,154,861 B2
(45) Date of Patent: Oct. 26, 2021

(54) FLUIDIC DEVICE FOR THE DETECTION, CAPTURE, OR REMOVAL OF A DISEASE MATERIAL

(71) Applicant: Vanderbilt University, Nashville, TN (US)

(72) Inventors: Sinead E. Miller, Houston, TX (US); Charleson S. Bell, Nashville, TN (US); Todd D. Giorgio, Nashville, TN (US); Andrew L. Cook, Antioch, TN (US)

(73) Assignee: Vanderbilt University, Nashville, TN (US)

( * ) Notice: Subject to any disclaimer, the term of this patent is extended or adjusted under 35 U.S.C. 154(b) by 205 days.

(21) Appl. No.: 16/315,732

(22) PCT Filed: Jul. 7, 2017

(86) PCT No.: PCT/US2017/041038
§ 371 (c)(1),
(2) Date: Jan. 7, 2019

(87) PCT Pub. No.: WO2018/009756
PCT Pub. Date: Jan. 11, 2018

(65) Prior Publication Data
US 2019/0240663 A1    Aug. 8, 2019

Related U.S. Application Data

(60) Provisional application No. 62/359,322, filed on Jul. 7, 2016, provisional application No. 62/407,767, filed
(Continued)

(51) Int. Cl.
*B01L 3/00*      (2006.01)
*A61M 5/165*   (2006.01)
(Continued)

(52) U.S. Cl.
CPC ........ *B01L 3/502753* (2013.01); *A61K 38/12* (2013.01); *A61K 38/14* (2013.01);
(Continued)

(58) Field of Classification Search
CPC .. B01L 3/502753; B01L 3/5027; B01L 3/502; B01L 3/50; A61K 38/12; A61K 38/14; A61M 5/165
(Continued)

(56) References Cited

U.S. PATENT DOCUMENTS

2002/0164816 A1    11/2002  Quake
2003/0152491 A1     8/2003  Kellogg et al.
(Continued)

FOREIGN PATENT DOCUMENTS

CN    1700009       11/2005
CN    103732271     4/2012
(Continued)

OTHER PUBLICATIONS

Zheng, Isolation of viable cancer cells in antibody-functionalized microfluidic device, Biomicrofluidics. Mar. 2014; 8(2): 024119. (Year: 2014).*
(Continued)

*Primary Examiner* — Christine T Mui
(74) *Attorney, Agent, or Firm* — Meunier Carlin & Curfman LLC

(57) ABSTRACT

The present disclosure relates to a fluidic device to detect, capture, and/or remove disease material in a biological fluid. The present invention also relates to methods for the treatment/prevention of sepsis through the use of the claimed device.

17 Claims, 18 Drawing Sheets

Related U.S. Application Data on Oct. 13, 2016, provisional application No. 62/454,235, filed on Feb. 3, 2017, provisional application No. 62/478,904, filed on Mar. 30, 2017.

(51) Int. Cl.
| | |
|---|---|
| *G01N 33/53* | (2006.01) |
| *G01N 33/543* | (2006.01) |
| *G01N 33/48* | (2006.01) |
| *A61K 38/12* | (2006.01) |
| *A61K 38/14* | (2006.01) |

(52) U.S. Cl.
CPC ....... *A61M 5/165* (2013.01); *B01L 3/502715* (2013.01); *B01L 3/502776* (2013.01); *G01N 33/48* (2013.01); *G01N 33/53* (2013.01); *G01N 33/543* (2013.01); *B01L 2300/0861* (2013.01); *B01L 2300/16* (2013.01)

(58) Field of Classification Search
USPC .......................................... 422/502, 500, 50
See application file for complete search history.

(56) References Cited

U.S. PATENT DOCUMENTS

| | | | | |
|---|---|---|---|---|
| 2009/0142772 | A1* | 6/2009 | Lau | G01N 33/54326 435/7.1 |
| 2012/0122831 | A1* | 5/2012 | Sauer-Budge | A61P 31/04 514/196 |
| 2014/0154703 | A1 | 6/2014 | Skelley et al. | |
| 2015/0038364 | A1* | 2/2015 | Zheng | C40B 20/02 506/9 |
| 2015/0285808 | A1 | 10/2015 | Sunitha et al. | |

FOREIGN PATENT DOCUMENTS

| | | |
|---|---|---|
| CN | 103889556 | 6/2014 |
| JP | 2003-265606 | 9/2003 |
| JP | 2007-268490 | 10/2007 |
| WO | 2006/021410 | 3/2006 |
| WO | 2009/012343 | 1/2009 |
| WO | 2010/092333 | 8/2010 |
| WO | 2010092333 | 8/2010 |
| WO | 2011/109762 | 9/2011 |
| WO | 2016/040850 | 3/2016 |
| WO | 2016040850 | 3/2016 |
| WO | 2016/077055 | 5/2016 |
| WO | WO 2019/241794 A1 * | 12/2019 ............... C12Q 1/02 |

OTHER PUBLICATIONS

International Search Report and Written Opinion dated Sep. 13, 2017, from International Application No. PCT/US2017/041038, 11 pages.
Extended EP Search Report dated Nov. 28, 2019, from related EP Application No. 17824950.4, 7 pages.
Bhagat, et al., Continuous particle separation in spiral microchannels using Dean flows and differential migration. Lab Chip 8, 1906-1914 (2008).
Boucher, et al., Bad bugs, no drugs: no ESKAPE! An update from the Infectious Diseases Society of America. Clin. Infect. Dis. 48, 1-12 (2009).
Eliopoulos, et al., Acinetobacter baumannii: epidemiology, antimicrobial resistance, and treatment options. Clin. Infect. Dis. 46, 1254-63 (2008).
Kang, et al., An extracorporeal blood-cleansing device for sepsis therapy., Nat Med., 20, 1211-1216 (2014).
Katsaragakis, S. et al. Acinetobacter baumannii infections in a surgical intensive care unit: predictors of multi-drug resistance. World J. Surg. 32, 1194-202 (2008).
Lee, et al., 3D-printed microfluidic device for the detection of pathogenic bacteria using size-based separation in helical channel with trapezoid cross-section, Sci Rep 5, 7717 (2015).
Mayr, et al., Epidemiology of severe sepsis, Virulence 5, 4-11 (2014).
Raub, C. B. et al., Sequestration of bacteria from whole blood by optimized microfluidic cross-flow filtration for Rapid Antimicrobial Susceptibility Testing, Sensors Actuators B Chem. 210, 120-123 (2015).
Sun, et al., Double spiral microchannel for label-free tumor cell separation and enrichment. Lab Chip 12, 3952-60 (2012).
Communication Pursuant to Article 94(3) EPC issued in related EP application No. 17824950.4, 6 pages, Oct. 13, 2020.
Office Action and Search Report dated Jul. 28, 2021. issued in related CN Application No. 2017800551627, 29 pages.

* cited by examiner

FLUIDIC DEVICE FOR THE DETECTION, CAPTURE, OR REMOVAL OF A DISEASE MATERIAL

CROSS REFERENCE TO RELATED APPLICATIONS

This application is a national stage application filed under 35 U.S.C. § 371 of PCT/US2017/041038 filed Jul. 7, 2017, which claims the benefit of U.S. Provisional Patent Application Ser. No. 62/359,322, filed Jul. 6, 2016, U.S. Provisional Patent Application Ser. No. 62/407,767, filed Oct. 13, 2016, U.S. Provisional Patent Application Ser. No. 62/454,235, filed Feb. 3, 2017, and U.S. Provisional Patent Application Ser. No. 62/478,904 filed Mar. 30, 2017, each of which are expressly incorporated herein by reference.

STATEMENT REGARDING FEDERALLY SPONSORED RESEARCH

This invention was made with Government Support under Grant No. W81XWH-13-1-0397 awarded by the Department of Defense. The Government has certain rights to the invention.

FIELD

The present disclosure relates to a fluidic device to detect, capture, and/or remove disease-causing material from biological fluids.

BACKGROUND

Many diseases, as well as disease associated cells and disease associated molecules, are blood-borne. For example, the presence of bacteria in the circulatory blood initiates a cascade of local and systemic regulatory mechanisms that can result in sepsis. Sepsis, defined as a life-threatening organ dysfunction caused by a dysregulated host response to infection, afflicts over one million Americans annually and has an associated mortality rate ranging from 25-50%. Sepsis is the leading cause of death in the critically ill in the United States, costing the US over $20 billion in treatment annually. As the average life expectancy increases and the number of invasive procedures expands, the incidence of sepsis is rising. Currently, no specific sepsis treatment is available. Treatment of sepsis relies primarily on early recognition and rapid administration of appropriate antibiotics, fluid resuscitation, and vasoactive medications. Early, effective antibiotic therapy is essential and improves patient outcomes. However, sepsis-associated mortality remains unacceptably and persistently high, which highlights the urgent need for new sepsis therapies.

Much research has been done to evaluate experimental adjunct treatments for sepsis, such as extracorporeal cytokine filtration, recombinant human activated protein C, corticosteroids, human recombinant lactoferrin, and immunomodulation. Although immunomodulation has been widely anticipated, the heterogeneity of the patient population and the complexity of sepsis pathogenesis have limited advancement of these experimental approaches. Blockage of single mediators, such as interleukin-1 (IL-1) or tumor necrosis factor-alpha (TNF-α), has shown little promise in improving sepsis survival. Cytokine removal has displayed encouraging results in animal studies. However, results are believed to be a consequence of modulating other downstream mechanisms rather than the direct impact of cytokine removal. Benefits of endotoxin clearance have also shown efficacy in animal studies, but have yet to demonstrate improvement of septic patient outcomes.

Mechanical bacterial removal using magnetic nanoparticles has been reported to improve survival of septic rodent models. Surface modification of nanoparticles using bacterial targeting ligands can lead to the efficient and reproducible capture of several important pathogenic bacteria. However, these approaches suffer from potential limitations in scale-up for treatment of large living systems and uncertain regulatory hurdles in regard to blood contact with nanoparticles. It also requires the incubation of bacterial cells with nanoparticles prior to separation. This incubation time allows bacteria to replicate and increase in number. Further, magnetic nanoparticles present in the blood may diffuse into organs and cause biocompatibility issues. Treatment addressing either a single molecular activator/inhibitor or isolation of the bacterial source is unlikely to sufficiently address the complexity of sepsis.

Current methods for treatment of bacteremia, or sepsis, also include the use of antibiotics. However, pathogens are rapidly gaining antimicrobial-evading capabilities or multidrug resistance, and systemic antibiotic administration is associated with a large number of negative side effects. Various adsorbents and other conventional membrane-filtration methods have been employed to detect or filter disease material from the blood, exploiting differences in cell size, deformability, and density to filter out target cells. However, these techniques are time consuming, labor-intensive, and require multistep sample preparations. Multistep sample preparation is a process susceptible to contamination and is not efficient enough for point of care treatment purposes. Membrane filtration methods present the problem of frequent clogging and require cleaning. Furthermore, filtration and centrifugation techniques cause stress to healthy cells that need to be returned to the patient. Hence, a simpler and more efficient technique is needed to process blood samples to remove disease materials and disease cells, while maintaining the original cell phenotype of healthy cells for subsequent return to the patient.

The fluidic devices and methods disclosed herein address these and other needs.

SUMMARY OF THE INVENTION

The inventors have engineered a device capable of both pathogen and endotoxin removal from whole, human blood, thereby addressing the two fundamental causes of dysregulated biological response in sepsis. This device can overcome the limitations of previous sepsis therapies that rely on removal of a single sepsis-related mediator from the blood. Removal of pathogens, including antibiotic-resistant strains, and endotoxins provides a new paradigm for the treatment of sepsis.

The device and methods described herein allow biological fluids, such as the entire blood volume of a patient, to be processed through the device several times during a single treatment. This permits the burden of the disease-causing material in the bloodstream to be significantly decreased by circulating the blood several times through the device. Removal of bacteria from the bloodstream can reduce the spread of infectious agents to distal sites. This reduces the number of pathogens present within organs or abscesses and decreases levels of inflammatory mediators.

Decreasing the total burden of the disease-causing materials can directly inhibit disease progression, and thus, this treatment can significantly extend the time available to identify, for example, the bacterial species causing infection, and begin optimal antibiotic therapy. Additionally, antibiotic therapy can be dually administered with this bacteria removal therapy because the ligand functionalized to the channel walls binds to both dead and live pathogens. The device can also be used to help accelerate pathogen identification and antibiotic susceptibility determination because large numbers of bacteria are captured within the device in a single pass.

Furthermore, this device can also be further modified to remove proteins (such as cytokines) as well as other types of cells (such as circulating tumor cells) from whole blood by functionalizing the channel walls with appropriate protein-specific or cell-specific ligands.

Still further, the device can be used to isolate and identify the disease-causing materials rather than relying on the device to substantially remove the disease-causing materials from the patient's blood stream. This focus on isolation and identification can permit the prompt formulation and commencement of a course of treatment.

Disclosed herein is a device for the detection, capture, and/or removal of disease causing material (for example, bacteria) from biological fluids.

Also disclosed herein are methods of treatment wherein such device is used in the separation of such disease-causing material from such biological fluids.

Still further, disclosed herein are methods of treatment wherein such device is used in the identification of disease causing material from biological fluids so that further subsequent courses of treatment may be formulated.

More specifically, disclosed herein is a fluidic device comprising:
at least one inlet;
at least one outlet;
a multidirectional channel between the at least one inlet and at least one outlet, said channel
comprising an inner wall; and
a ligand coating at least a portion of the inner wall of the multidirectional channel.

Also disclosed is a method for the capture and removal of a disease material from a biological fluid, said method comprising the steps of:
introducing the biological fluid into a fluidic device, wherein the fluidic device comprises at least one inlet, at least one outlet, and a multidirectional channel between the at least one inlet and the at least one outlet;
flowing said biological fluid through said fluidic device to focus and expose said disease material to a disease material-targeting ligand functionalized along an inner wall of the channel within the fluidic device;
capturing the disease material through the binding of the disease material with a disease material-targeting ligand bound to the inner wall of the channel; and
removing said disease material from said biological fluid.

Still further, disclosed herein is a method for extracorporeal capture and removal of a blood-borne disease material from blood by which treated blood is returned to a patient, said method comprising the steps of:
pumping blood from a patient into a fluidic device, wherein the fluidic device comprises at least one inlet, at least one outlet, and a multidirectional channel between the at least one inlet and the at least one outlet;
flowing said blood through said fluidic device to focus and expose said blood-borne disease material to a disease material-targeting ligand functionalized along an inner wall of the channel within the fluidic device;

focusing and capturing the disease material, wherein a force imposed by the fluidic device focuses the disease material near a wall of the channel that is functionalized with the disease material-targeting ligand, which then binds to said disease material;
removing said disease material from said blood to produce treated blood; and
returning said treated blood to said patient.

Still further, disclosed is a method for capture and detection of a blood-borne disease material from blood, said method comprising the steps of:
flowing blood into a fluidic device to focus and expose said blood-borne disease material to a disease material-targeting ligand functionalized along an inner wall of a channel within the fluidic device; wherein the channel within the fluidic device comprises a spiral channel;
capturing the disease material, wherein a force imposed by the fluidic device focuses the disease material near a wall of the spiral channel that is functionalized with the disease material-targeting ligand, which then binds to said disease material;
flowing optically-active, disease material targeting microbeads through the fluidic device which bind to said disease material; and
reading the fluidic device with an optical reader.

Still further, disclosed is a composition of matter comprising a biological fluid which has flowed through a fluidic device, wherein the fluidic device comprises at least one inlet, at least one outlet, and a multidirectional channel between the at least one inlet and the at least one outlet, said channel comprising an inner wall having a ligand coating at least a portion of said inner wall, wherein such ligand binds to and removes a disease material from said biological fluid.

Still further, disclosed herein is a method for extracorporeal capture and removal of a disease material from blood by which treated blood is returned to the body, comprising the steps:
pumping blood from a patient into a spiral-based fluidic apparatus;
flowing said blood through said spiral-based fluidic apparatus to focus and expose said disease material to a disease material-targeting ligand functionalized along the spiral fluidic apparatus inner walls;
focusing and capturing the disease material, wherein size-based inertial forces imposed by the spiral-based fluidic apparatus focus the disease material near the walls of a spiral channel that is functionalized with a disease material-targeting ligand, which then binds to said disease material;
removing said disease material from said blood; and
returning said blood to said patient.

Still further, disclosed herein is a method for capture and detection of a disease material from blood, comprising the steps:
flowing blood into a fluidic apparatus to focus and expose said disease material to a disease material-targeting ligand functionalized along the fluidic apparatus inner walls;
focusing and capturing the disease material, wherein size-based inertial forces imposed by the fluidic apparatus focus the disease material near the walls of a spiral channel that is functionalized with a disease material-targeting ligand, which then binds to said disease material;

flowing optically-active, disease material targeting microbeads through the fluidic apparatus which bind to the said disease material; and reading the fluidic apparatus with an optical reader.

BRIEF DESCRIPTION OF THE DRAWINGS

The accompanying figures, which are incorporated in and constitute a part of this specification, illustrate several aspects described below.

FIG. 1A is a schematic of the multidirectional fluidic device containing 6-loop double spiral channels with one inlet and three outlets for particle/bacteria capture. FIG. 1B is a schematic representation of the multidirectional channel separating bacteria through interaction with the bacteria-targeting ligand. Colistin-PEG-Silane (Col-PEG-Si), bond to the inner walls of the microchannel.

FIG. 2A is a schematic representation of the Colistin-PEG-Silane (Col-PEG-Si) coated inner channel walls. FIG. 2B shows the molecule colistin which contains five amine groups, one of which is used to conjugate to PEG, resulting in the Col-PEG-Si ligand, thereby leaving four remaining amine groups to interact and bind the bacteria cells within the microchannel. FIG. 2C shows the microchannel imaged using fluorescent microscopy following the Col-PEG-Si capture of bacteria and subsequent exposure to an Atto 488 amine dye.

A. baumannii ATCC17978 capture from whole, human blood following passage through colistinated device at 0.2 mL min$^{-1}$ and subsequent washing. d, Lack of green fluorescently labeled S. aureus ATCC29213 capture following passage through the colistinated device at 0.2 mL min$^{-1}$, confirming specificity for Gram-negative pathogens in colistin-functionalized devices.

Figure 17:
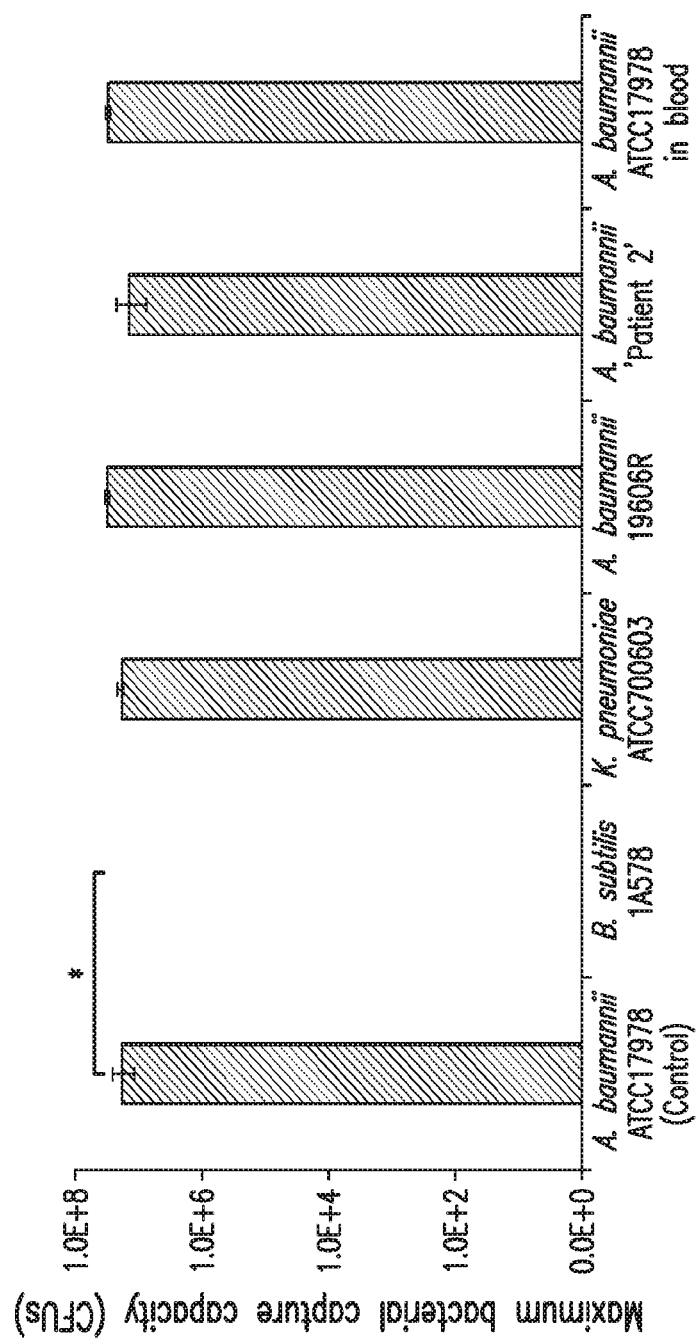

FIG. 17 shows the total bacterial capture capacity of a certain colistinated double spiral fluidic device within the scope of the present invention. The maximum bacterial load that such device can capture is reported with respect to each bacterial strain indicated. A. baumannii ATCC17978 spiked in PBS served as the control. Capture of A. baumannii ATCC17978 was significantly different than the capture of B. subtilis 1A578. However, the capture of A. baumannii ATCC17978 was not significantly different than any other bacterial isolate listed. The maximum capture capacities of all other bacterial isolates listed (K. pneumoniae ATCC700603, A. baumannii 19606R, A. baumannii 'Patient 2', and A. baumannii ATCC17978 in blood) were also significantly different that of B. subtilis 1A578. Data were compared using one-way ANOVA followed by post hoc Tukey's multiple comparison test. Results are plotted as mean±SD, n=3. *P<0.01.

Figure 18:
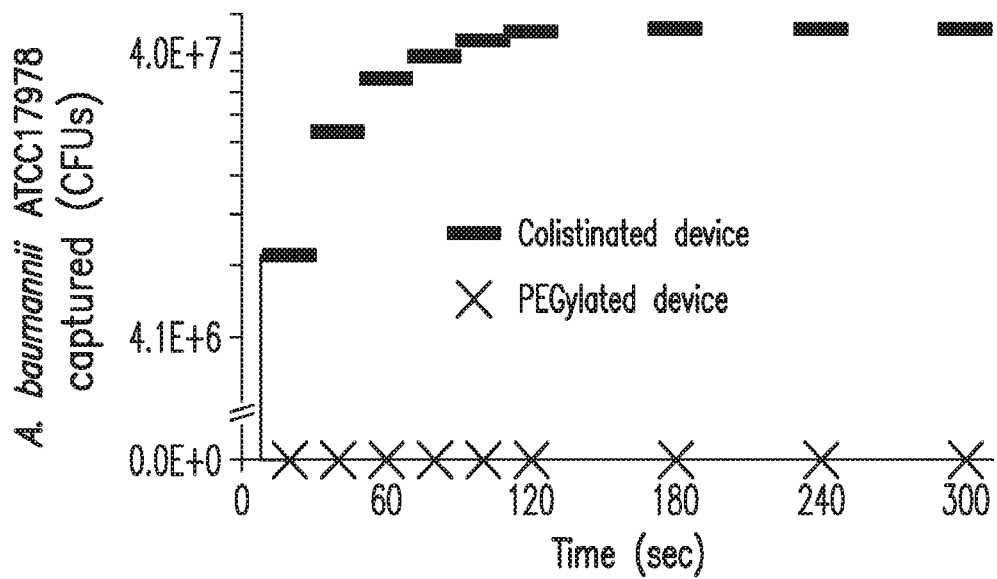

FIG. 18 reveals the bacterial capture capacity of a double spiral fluidic device that is larger than that use in FIG. 17. A. baumannii ATCC17978 spiked into PBS was flowed through a colistinated and PEGylated double spiral microfluidic device (328 mm L×750 μm W×15 μm H) at 0.6 mL min$^{-1}$. The A. baumannii ATCC17978 capture capacity of the microfluidic device was quantified over the time indicated. Results are plotted as the mean±SD, n=3. *P<0.01.

Figure 19:
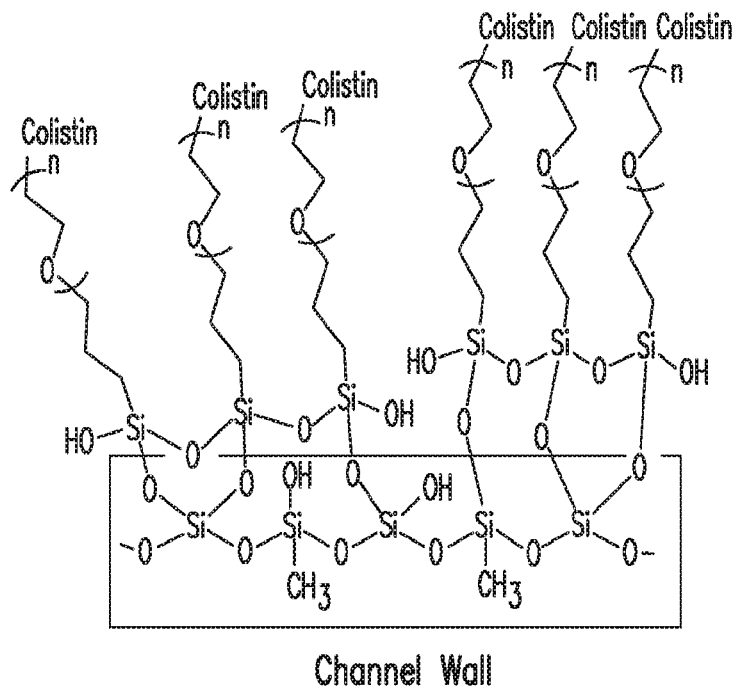

FIG. 19 shows a schematic description of colistin immobilization onto the microchannel walls. NHS was used to couple Silane-PEG-NHS to one of the five similarly reactive L-α-diaminobutyric acid (Dab) residues of colistin through the amine side chain of Dab[32]. The NHS group of Silane-PEG-NHS covalently binds to any single, comparably reactive amine residue of the colistin antibiotic via carbodiimide chemistry, resulting in Colistin-PEG-Silane. The silane end of Colistin-PEG-Silane forms siloxane bonds to the PDMS-based channel walls, resulting in colistin being extended into the lumen of the channel.

Figure 20:
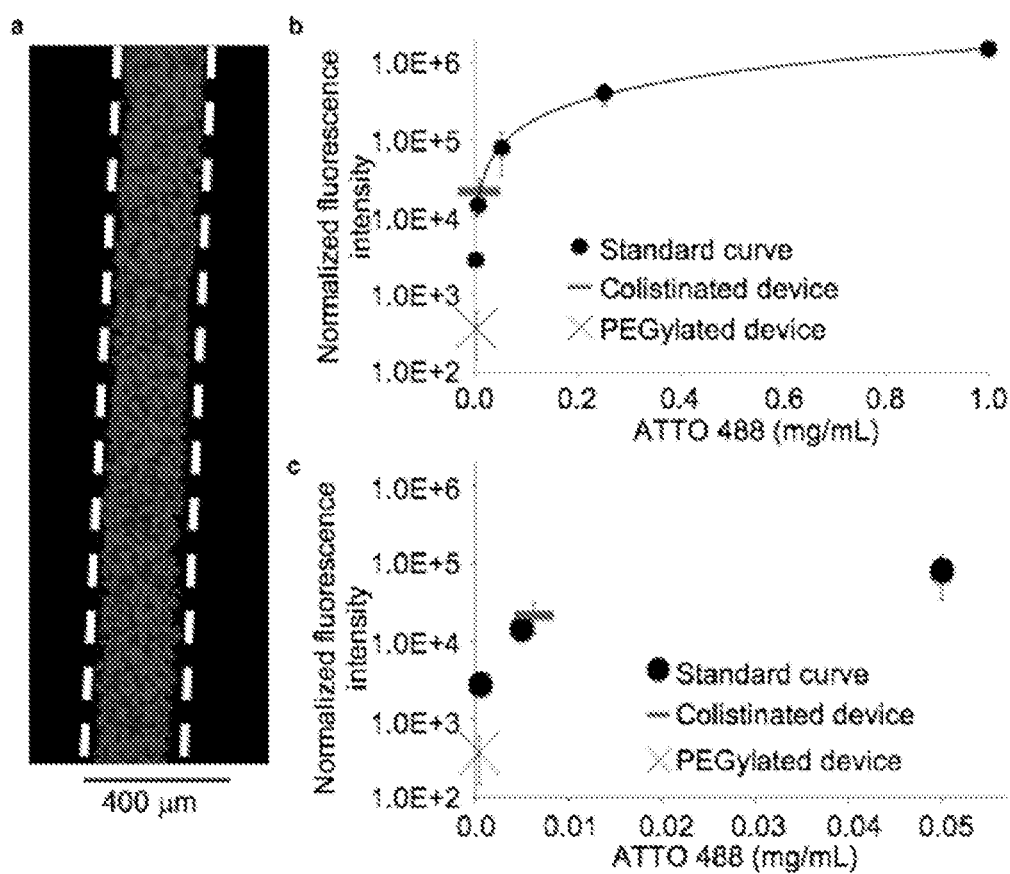

FIG. 20 provides confirmation of colistin decoration within microchannel a, Fluorescent labeling of the amine groups of colistin was carried out with ATTO 488 NHS ester dye. The ATTO 488 NHS ester dye was added to a colistinated device and then washed with PBS. Staining indicates the presence of colistin within the microchannel b, Standard dilutions of ATTO 488 NHS ester in DMSO were used to generate a standard fluorescence curve. c, Fluorescence generated from ATTO 488 NHS ester stained colistinated device and ATTO 488 NHS ester PEGylated device were compared to the standard curve. It was determined that 1.76 μg of colistin are present within the colistinated double spiral device. Results are plotted as the mean±SD, n=3.

Figure 21:
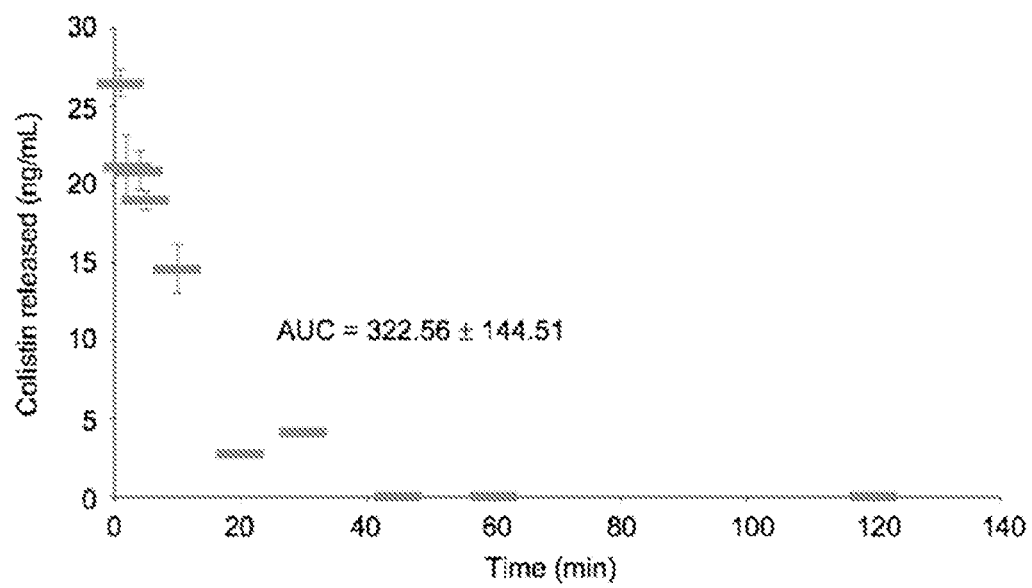

FIG. 21 shows colistin ligand retention within the a device within the claimed invention having a double spiral microchannel configuration. The release of colistin from the colistinated device was analyzed using a colistin ELISA (Bio Scientific). PBS buffer was continuously flowed through a colistinated microfluidic device at 0.2 mL min$^{-1}$. The fluid was captured from the outlet at the time points indicated to analyze the possible detachment of colistin from the channel walls. Under continuous flow, 300 ng of colistin were released from the channel over the course of 2 hours. These levels of colistin are non-toxic. Importantly, no colistin was detectable in the outlet flow after approximately 40 minutes, making feasible a wash to remove uncoupled colistin from the device before use. Results are plotted as the mean±SD, n=3.

Figure 22:
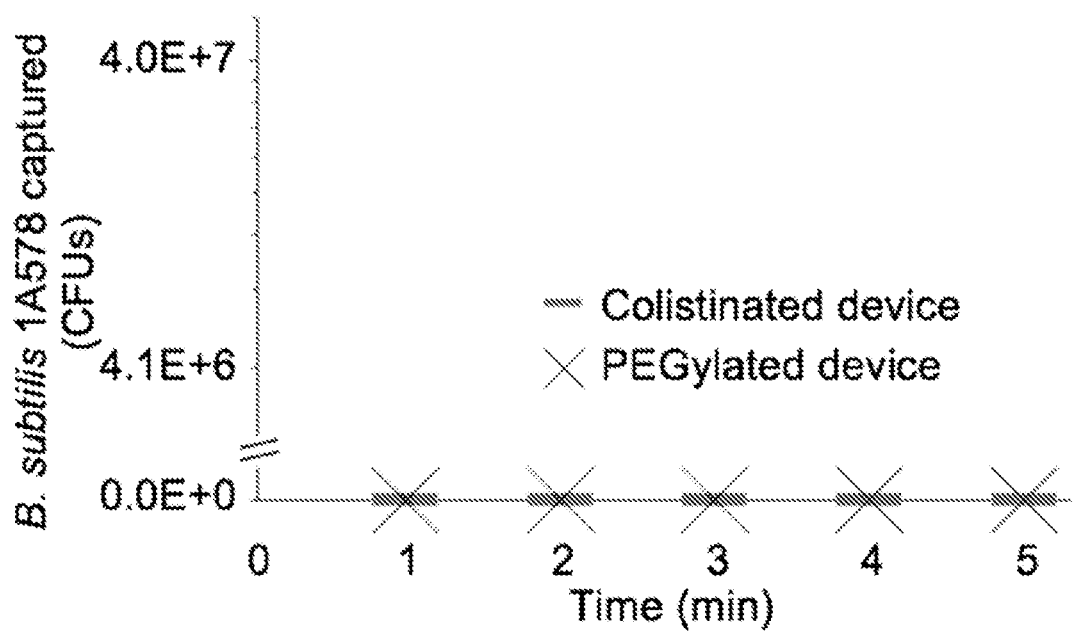

FIG. 22 depicts the evaluation of Gram-positive bacterial capture. Pathogen capture capacity of Gram-positive B. subtilis 1A578 when spiked into PBS and flowed through the colistinated and PEGylated double spiral microfluidic device at 0.2 nil min$^{-1}$, The lack of capture indicates the specificity of colistin for Gram-negative pathogens. Results are plotted as the mean±SD, n=3.

Figure 23:
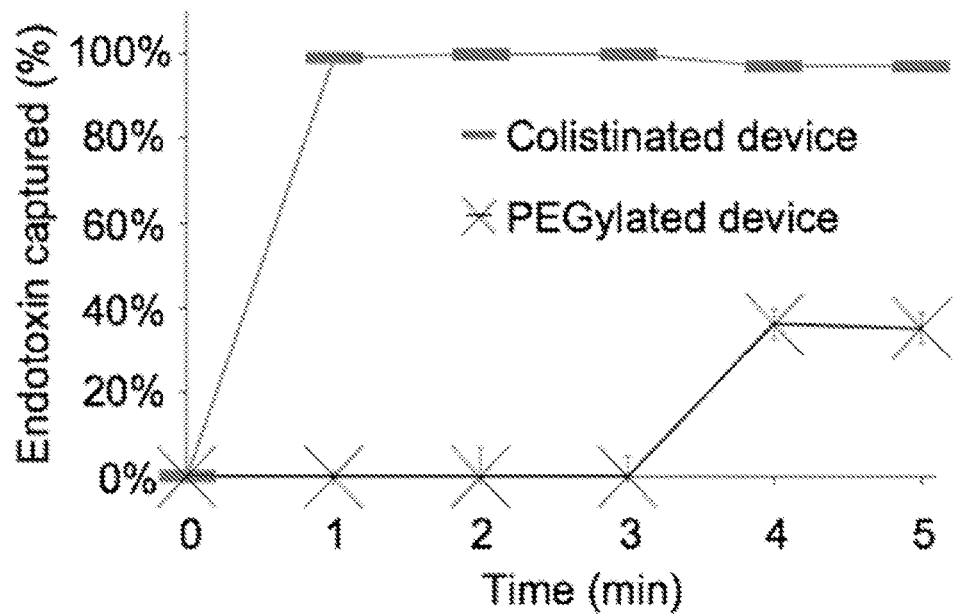

FIG. 23 provides quantification of endotoxin capture capacity. Endotoxin was spiked into endotoxin-free water (1 EU ml$^{-1}$) and flowed through a colistinated and PEGylated double spiral fluidic device at 0.2 ml min$^{-11}$. The amount of endotoxin captured over time was assessed. Results are plotted as the mean±SD, n=3.

Figure 24:
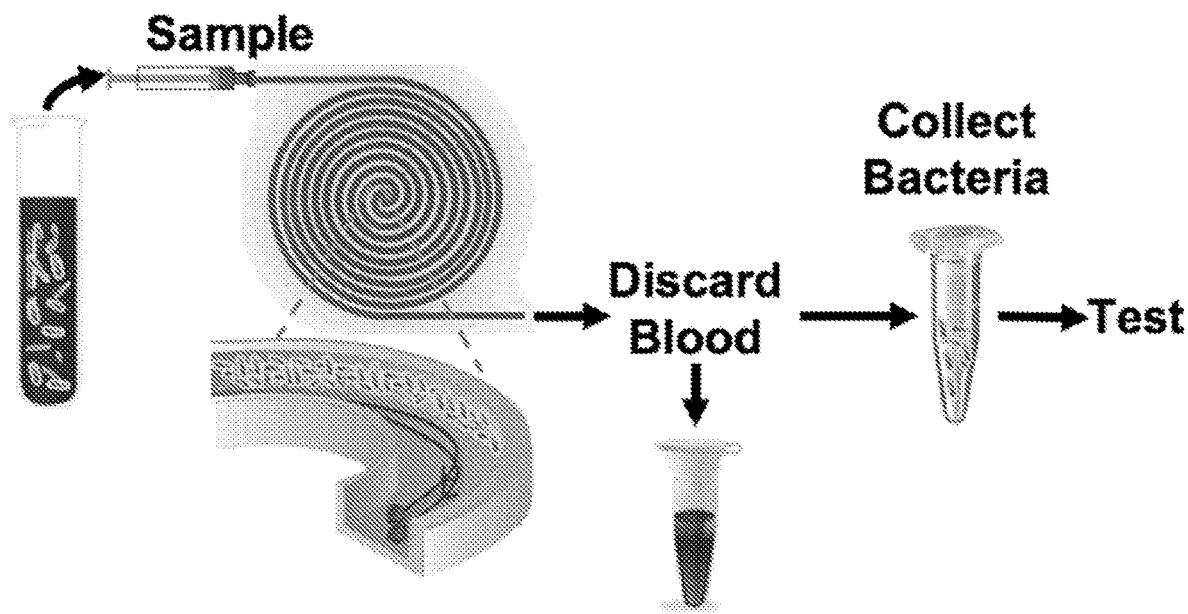

FIG. 24 is an illustration of blood containing disease material (i.e. rod-shaped cells) being pumped through a tube to the spiral-based fluidic apparatus, which is functionalized along the channel walls with disease material-targeting ligands designed to capture disease material.

Figure 25:
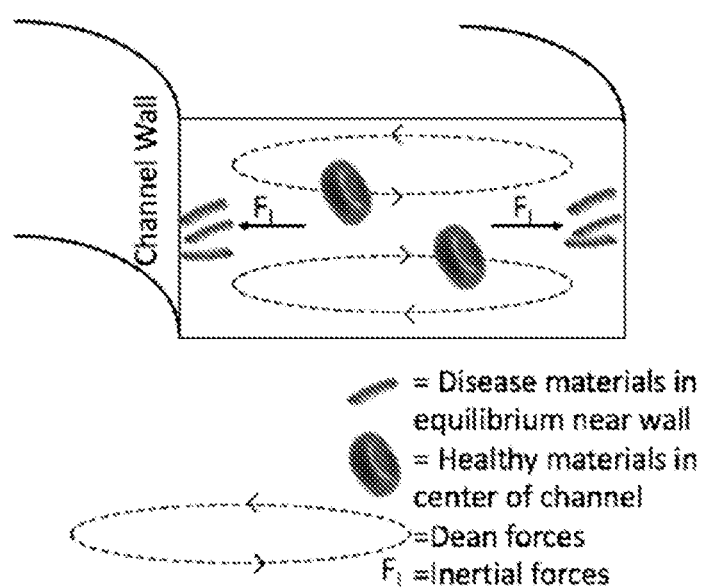

FIG. 25 is a schematic depiction of the forces within a spiral-based fluidic apparatus channel Due to channel curvature, the two counter-rotating Dean forces are orthogonal to the main flow direction. Dean force causes recirculation of desired, healthy materials (i.e. red, blood cells) in the center of the channel. The disease material (i.e. green, disease material) are subject to inertial lift force, which focuses the targeted disease material near the ligand functionalized channel walls, as the healthy materials remain free in the channel center lumen.

Figure 26:
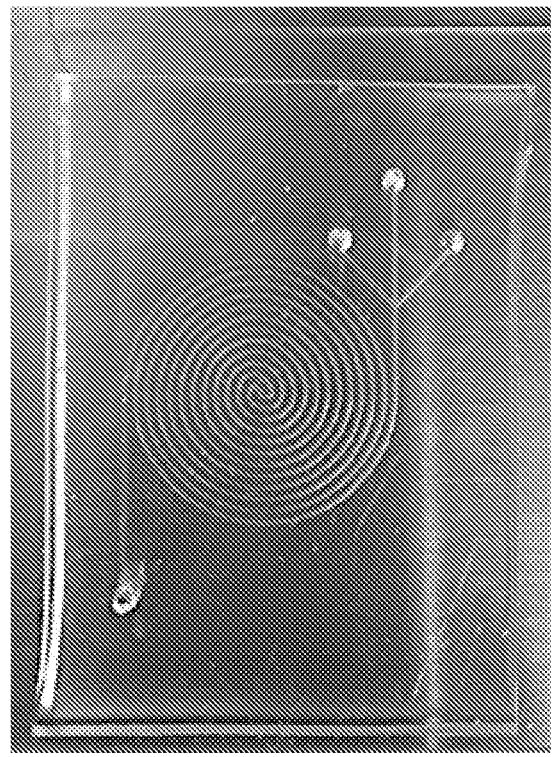

FIG. 26 is an illustration of a polymethyl methacrylate (PMMA) fabricated fluidic device designed to target and capture disease material, in accordance with an embodiment of the present invention.

Figure 27:
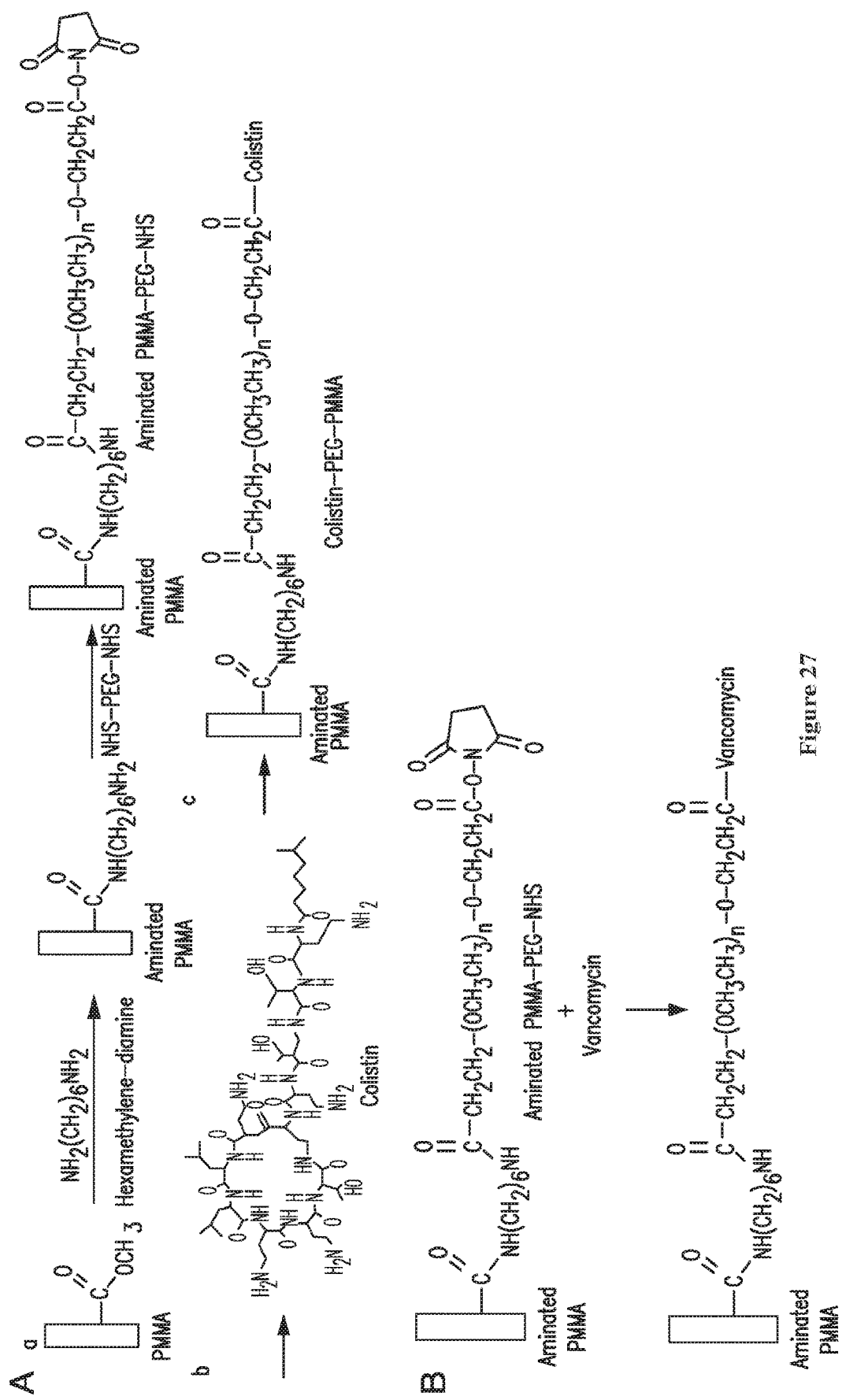

FIG. 27 is an illustration of the formation of a fluidic apparatus wall composed of disease material-targeting ligand. The formation of (A) colistin and (B) vancomycin disease material-targeting ligands in accordance with an embodiment of the present invention.

Figure 28:
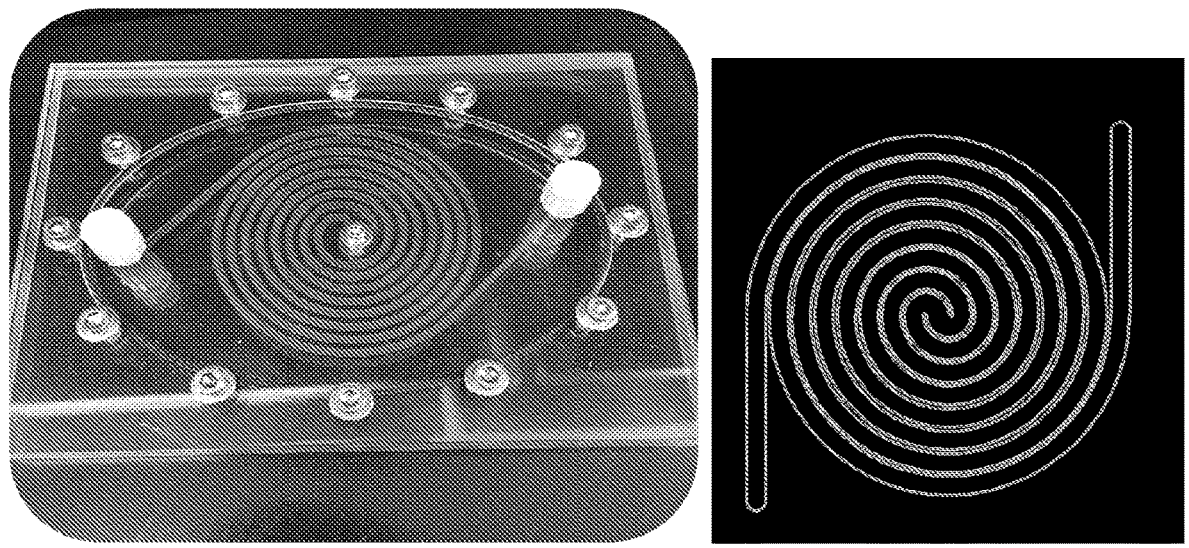

FIG. 28 is an illustration of a scaled-up version of the present invention fabricated form polycarbonate.

Figure 29:
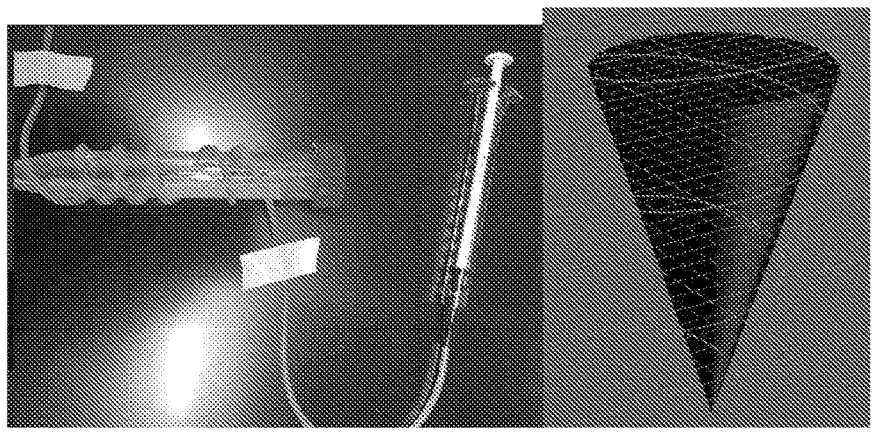

FIG. 29 shows an alternative embodiment of the present fluidic device. The specimen or biological fluid is pumped/flowed through the helically wrapped channel, which for example, could be tubing. The channel is coated with disease material targeting ligand, allowing for the capture of disease material, such as pathogens.

DETAILED DESCRIPTION

Disclosed herein are fluidic devices and methods for the detection and capture of disease causing material. In some aspects, disclosed herein are systems and methods to remove unwanted disease materials from blood by focusing and separating specific disease materials away from desired blood materials within a spiral-based fluidic apparatus to avoid clogging issues associated with current filter membrane methods.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

As used herein in reference to the channel component within the claimed device, "multidirectional" means that the direction of the channel changes at least once. Such change in direction is necessary to increase the contact of the disease-causing materials with the ligands that line the inner wall of the channel. It is preferred that the multidirectional channels of the claimed device contain multiple changes of direction. This can be accomplished through the use of a multitude of configurations, some of which are specifically disclosed in this specification. Nonlimiting examples of multidirectional channels include the use of a double spiral (e.g. FIG. 1, FIG. 8) or a curve (FIG. 4B, FIG. 16B). However, it should be understood that the claimed invention is not limited to the exemplified configurations as other examples include a partial circle or a helix, which are also within the scope of the invention.

As used herein, "ligand" means any substance that forms a complex with a disease-causing material.

As previously stated, the fluidic device is comprised of:
at least one inlet to the fluidic device;
at least one outlet;
a multidirectional channel between the at least one inlet and at least one outlet, said channel comprising an inner wall; and
a ligand coating at least a portion of the inner wall of the multidirectional channel.

The size of the device is not critical to its function. However, the device should be sized such that the available area of the coated inner walls of the multidirectional channel (and therefore the length of the channel) are adequate for its intended usage. This may be accomplished by adjusting the size of the device or utilizing multiple devices in series and/or parallel configurations. In certain configurations, wherein the channel is present in only one plane, the height of the device can be very small, for example only about 15 μm.

Although not wishing to be limited to the following suggested size ranges, the length of the multidirectional channel may generally be in the range of 0.0005 to 1000 cm in size. Preferably, the device is in the range of 0.1 to 500 cm in size. Most preferably, the device is in the range of 0.1 to 100 cm in size. The overall size of the device is not critical and will be determined in large part by the particular configuration of the multidirectional channel.

The multidirectional channel within the claimed devices should also be sized in accordance with its intended use. For example, if the fluids intended for use therein are to contain whole cells or cell fragments, the diameter of the channel must be sized as to accommodate their passage and allow for the anticipated interaction with the ligand coating therein while avoiding clogging issues. If the intended fluids are to contain smaller disease-causing materials, for example, the diameter of the channel may be decreased in size. Although not wishing to be limited to the following suggested size ranges, the diameter of the channel within the device may generally be in the range of 0.001 to 1000 cm in size. Preferably, the device is in the range of 0.001 to 100 cm in size. Most preferably, the device is in the range of 0.01 to 30 cm in size. Some of the devices shown in the Figures and/or discussed in the Examples utilize channels having a diameter of about 0.5 cm.

The claimed device possesses at least one inlet and at least one outlet to the multidirectional channel. Again, the selection of the number of inlets and outlets is not critical but rather may be varied to optimize the performance of the device for its intended use. While not wishing to be bound to the following range of inlets, the number of inlets may typically vary from one to three. Preferably, the device will contain one to two inlets. Most preferably, the device will have only one inlet. In the case of outlets, the device will typically possess from one to five outlets. Preferably, it will possess from one to three outlets. Most preferably, the device will have one outlet.

The claimed device can be composed of any biocompatible material. The preferred biocompatible materials are polypropylene, polytetrafluoroethylene (PTFE), polymethyl methacrylate (PMMA), polydimethylsiloxane, acrylonitrile butadiene styrene, PEEK polymers, polyethylene, perfluoroalkoxy, glass, poly(etherketoneketone), polystyrene, polyolefin copolymers, graphene, metals, PolyChloroTriFluoroEthylene, polyacetal, polyurethane, polyarylethersulfone, polyvinylpyrrolidone, polyesters, polyvinyl chloride, cyclo olefin copolymers, polyamide, polysulfone, fluoropolymers, ethylene-vinyl acetate expanded PTFE (ePTFE), polyglycolic acid (PGA), polyglycolide-cotrimethylene carbonate (PGA-TMC), PGA-caprolactone, poly (lactic-co-glycolic) acid (PLGA), other plastics, polydimethylsiloxane (PDMS), SU-8, polyimide, paralyne, or combinations thereof. The most preferred biocompatible materials are silicone and polycarbonate.

The claimed device can be made through the employment of any number of technologies. For example, it may be made through 3-D printing, lithography, injection molding, blow molding, casting, ultrasonic welding, high frequency welding, heated tool or plate welding, solvent bonding, laser welding, spin welding, infrared welding, vibration welding, adhesive bonding, and machining. In some embodiments, the preferred machining methods are turning, drilling, boring, reaming, electric discharge machining and/or milling. Material may be machined to create an enclosure of desired dimensions, such as by machining channel(s) as a whole or by machining halves that may be attached. For the channel(s), silicone may be installed, and the inlet(s) and outlet(s) may be closed by caps. The machining may be performed on various biocompatible materials including various grades of polycarbonate. The device may then be coated with a ligand that is coating at least a portion of an inner wall of the multidirectional channel(s) through conventional means.

The claimed device may be used to remove and/or detect many types of disease-causing materials such as cancer cells, circulating tumor cells, peptides, beta amyloid, proteins, enzymes, toxins, diseased cells, cancer cells, infectious microorganisms, cells, parasites, fungi, viruses, microorganisms, bacteria, bacterial toxin, lipopolysaccharide, cytokines, IL-Iβ, IL-4, IL-6, IL-8, IL-10, IL-11, IL-13, IL-15, IL-16, tumor necrosis factors, procalcitonin, pathogen-associated molecular patterns, C reactive protein, quorum sensing proteins or receptors, or a small or protein bound biological molecule relevant to liver failure, or a combination thereof.

The fluidic device is functionalized along at least a portion of the inner walls of the multidirectional channel with ligands to capture disease-causing material and other material that is desired to be removed from a biological fluid such as blood. The ligands useful in the practice of the present invention include binding materials comprising antibodies, peptides, proteins, antibiotics, polymers, aptamers, ligands, tumor necrosis factors, adhesion receptors, E-selectin, cytokines, chemotherapy agents, quorum sensing proteins or receptors, and biological agents.

The ligands can be coated on the inner walls of the multidirectional channel by conventional means. The inner walls of the channel may be coated with a single type of ligand or mixtures thereof depending upon the intended use of the device. The extent of the coating on the inner walls can also vary. For example, the entire length of the inner walls of the microchannel may be coated or only a portion thereof.

The use of a multidirectional channel is important in the practice of this technology as it appears to result in increased contact between the disease-causing materials and the ligands lining the inner walls of the microchannel. While not wishing to be limited to the following, it is theorized that Dean vortex forces as described below are in operation within the multidirectional channels of the claimed device.

In laminar Poiseuille flow, the hyperbolic velocity profile has a maximum velocity at the centroid of the channel and zero velocity at the walls of the channel. The lift forces ($F_L$) acting on particles are dominated by wall-induced ($F_1$) and shear-induced ($F_2$) lift forces. These lift forces act in conjunction to yield a particle equilibrium position between the channel wall and centerline where the oppositely directed lift forces are equal and generate narrow particle bands. The net lift force ($F_L$) that cause particles to migrate away from the channel center and walls is estimated as, $F_L = f_L(Re, x_L) \rho U_m^2 a^4 / D_h^2$, where the lift coefficient ($f_L$) is a function of the channel Reynolds number Re ($Re = \rho U_m D_h / \mu$) and the particle position ($x_L$) within the cross-section of the channel $D_h$ is the microchannel hydraulic diameter, $\rho$ and $\mu$ are the density and viscosity of fluid, $U_m$ is the maximum fluid velocity, and a is the particle diameter.

Figure 1:
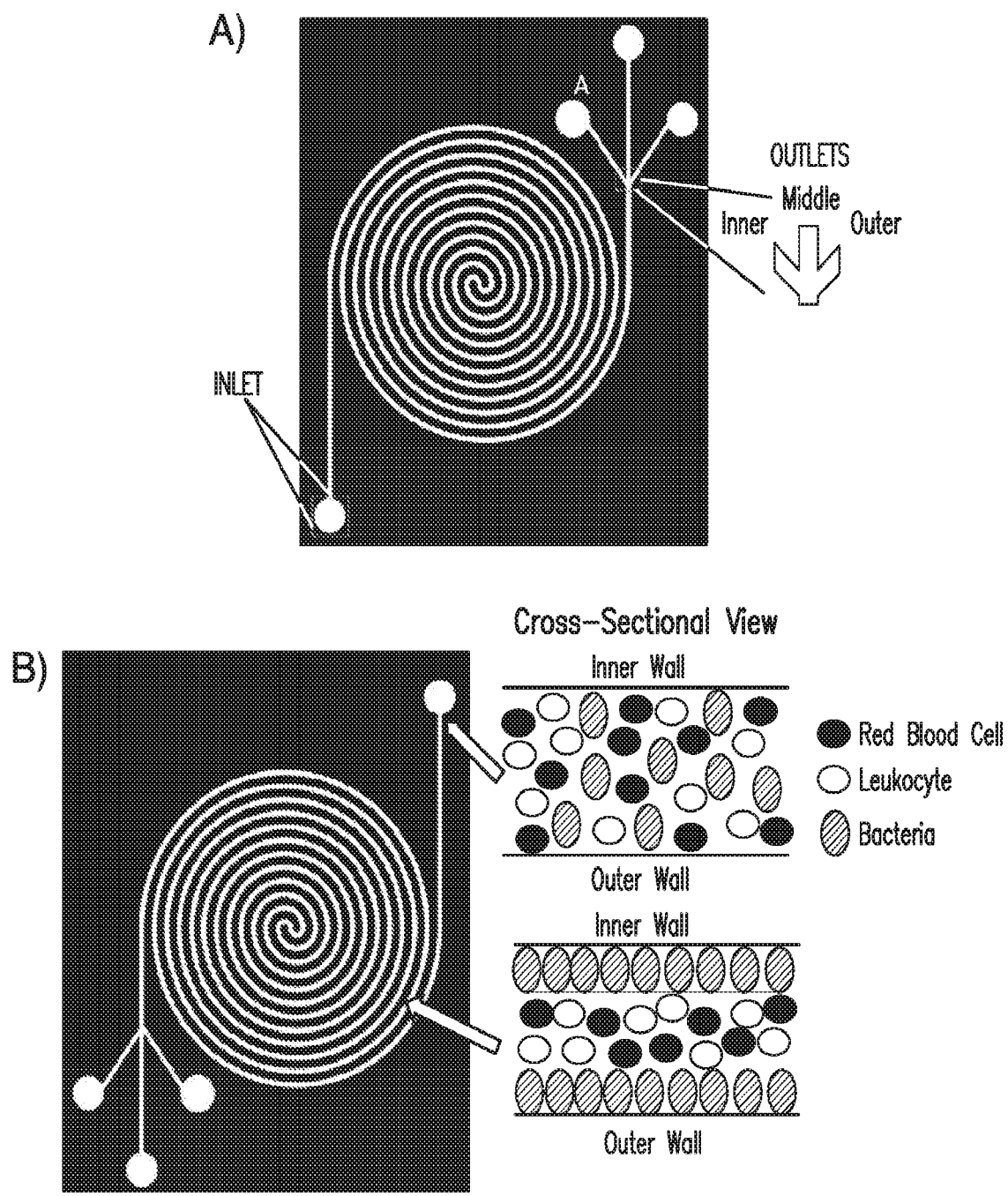
FIG. 1 contains schematics of various multidirectional fluidic devices within the scope of this invention.

However, in curved microfluidic channels, non-uniform inertia of fluid results in the development of secondary transverse flows, or Dean vortex flows, in the top and bottom halves of the channel (FIG. 1). The dimensionless Dean number (De), used to characterize the Dean vortex flow in a curved microchannel, can be defined as, $De = (\rho U_f D_h / \mu)\sqrt{(D_h/2R)}$, where R is the radius of curvature and $U_f$ is the average fluid velocity[31]. Assuming Stokes drag, the magnitude of the Dean drag force ($F_D$) exerted on particles due to these flows can be estimated by $F_D \sim 5.4*10^{-4} \mu\pi De a$.

Figure 13:
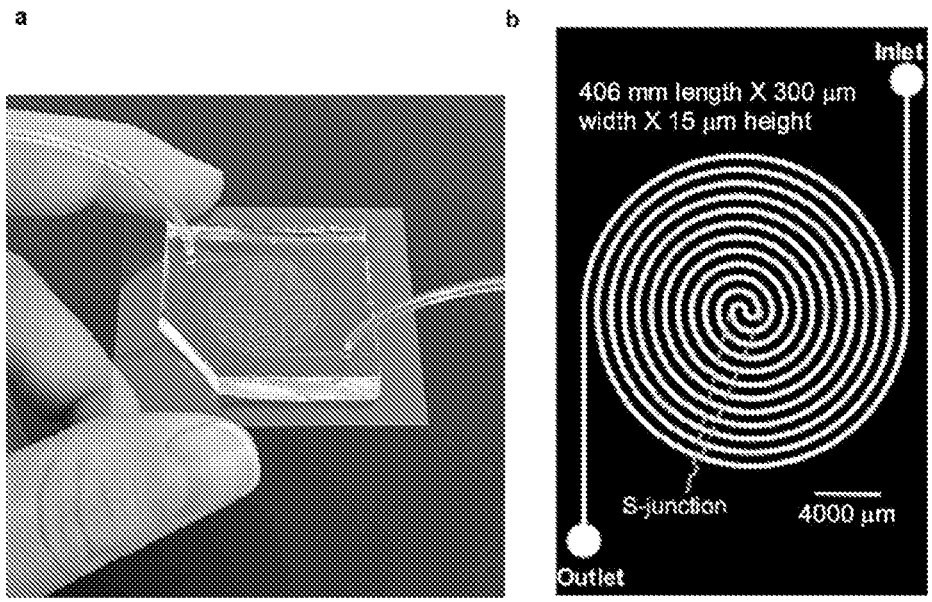
FIG. 13 shows a double spiral fluidic design to maximize bacterial separation efficiency. (a) A fabricated polydimethylsiloxane (PDMS) fluidic device is shown which consisting of two, 6-loop spiral microchannels joined at the S-junction to form a double spiral channel with one inlet and one outlet (b) A CAD drawing of the double spiral fluidic module employed to create the master mold is shown.

The equilibrium positions of particles in flow are primarily determined by the interactions between lift forces and Dean drag force. The double spiral geometry which is used in some embodiments of the present invention was formulated to cause disease-causing materials to occupy equilibrium positions near the inner microchannel walls when exposed to a flow rate of 0.2 mL min$^{-1}$. This allows the material to come in close proximity to the ligand functionalized microchannel walls, which leads to capture of the disease-causing material. To accomplish this, a double spiral microchannel was dimensionally designed to have, for example, a 406 mm length (L), 300 μm width (W), and 15 μm height (H) with six spiral loops for each direction (FIG. 13). This was intended to accomplish hydrodynamic separation and capture of bacteria and endotoxin in a curved geometry. The double spiral microchannel described has a low aspect ratio (H/W=0.05). The low aspect ratio of the microchannel rapidly forces disease-causing materials to migrate to final equilibrium positions.

Two μm sized particles (a/H~0.13; $F_L>F_D$) and 10.2 μm particles (a/H~0.67; $F_L>F_D$) under continuous flow conditions within a double spiral microchannel demonstrate that 2 particles are more influenced by inertial lift forces rather than Dean force, and thus equilibrate within the microchannel (FIGS. 14a and 14b) Particles that satisfy a/H≥0.07 are able to focus and occupy a single equilibrium position within a microchannel. The low aspect ratio of the channel design is believed to promote the focusing of smaller particles near the inner channel wall. The larger 10 μm sized particles equilibrate near the center of the channel due to the larger wall-induced lift force experienced, in comparison to 2 μm particles.

Figure 14:
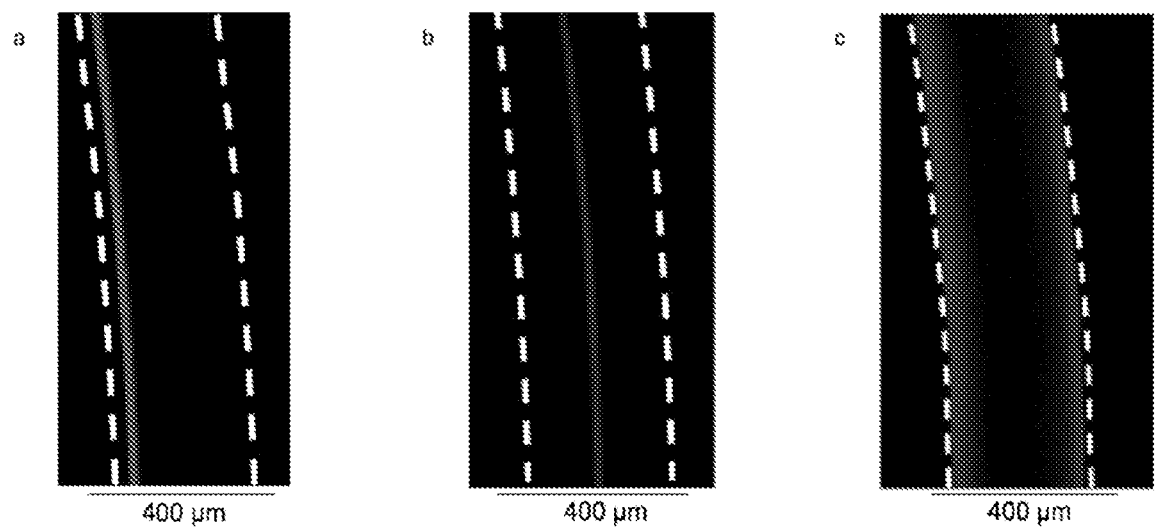
FIG. 14 shows a microparticle and bacterial focusing within a double spiral channel configuration of the claimed device. Images were acquired at a continuous flow rate of 0.2 mL min$^{-1}$. (a) focusing of 2 μm particles; (b) focusing of 10 μm particles; and (c) labeled *A. baumannii* ATCC17978 focusing along both the inner and outer walls of the double spiral microfluidic device.

Focusing positions of non-spherical particles are dependent on the particle's largest cross-sectional dimension. *A. baumannii* ATCC17978, a rod-shaped (coccobacillus) bacterium, is typically 2 μm in length and 0.5 μm in width. Hence, 2 μm particle focusing was evaluated (FIG. 14a). However, non-spherical bacterial cells can freely rotate and experience strong rotational-induced lift forces while being inertially focused and sorted. At Reynolds numbers greater than 10, both spherical and rod-shaped particles generally follow the same focusing trend. However, in microchannels with a low aspect ratio, such as the case with this design, rod-shaped particles focus to two equilibrium regions (FIG. 14c). Bacteria oscillate when close to the channel wall due to the rotational forces imposed on the rod-shaped particles. Near-wall focusing combined with rotation inducing lift forces presumably allow for direct contact of bacteria with both the inner and outer colistin functionalized channel walls.

The use of a spiral-based design (spiral channel), as is done within some embodiments of the present invention further imposes size-dependent inertial forces to aid in the capture of disease material from biological fluid passed through the claimed device.

Flow rates through the device can be optimized through conventional techniques depending upon the length and diameter of the multidirectional channel, the biological fluid that is to pass therethrough and the intended function of the device. Flow rates of about 0.2 mL/min to about 200 mL/min were utilized in the use of some of the devices exemplified herein.

It is also within the scope of this invention to arrange multiple versions of the claimed device in series or parallel configurations. Such devices can be identical or different in size, ligand coating, etc.

As previously noted, the claimed device comprises at least one input and at least one output. Both the provision of biological fluid to the device's input(s) and the removal of fluid from its output(s) may be accomplished with conventional means. Suitable pumps may be used for the introduction of fluid into the device and suitable collection means, such as vessel, containers, test tubes, may be used to collect fluid emerging from the output(s).

Figure 6:
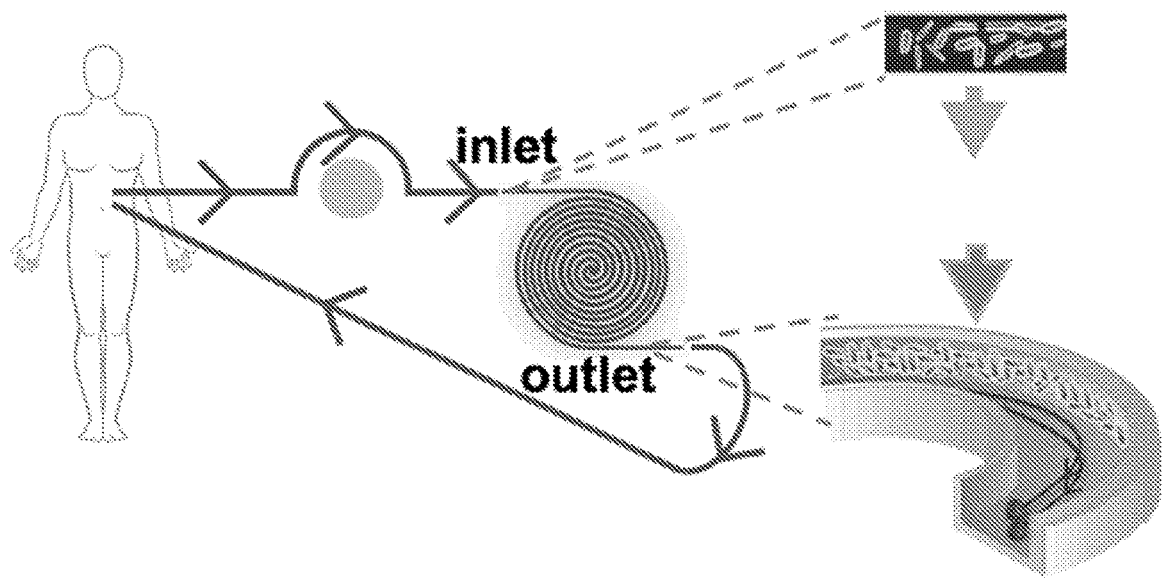
FIG. 6 is an illustration of blood containing disease material (i.e. rod-shaped cells) being pumped from a patient through a tube to the claimed fluidic apparatus, which is functionalized along the channel walls with disease material-targeting ligands designed to capture disease material. Following processing through the claimed fluidic apparatus, the blood containing healthy material is returned to the patient.

In some embodiments of the present invention, such as shown in FIG. 6, the biological fluid (here a patient's blood) is moved by a blood pump and flowed through the claimed device. Rather than being collected after emerging from the device, the patient's blood is instead reintroduced into the patient. The walls of the channel are, in this exemplary case, functionalized with a bacteria-targeting ligand (FIG. 6), thereby allowing for bacteria capture and removal. In this embodiment, the bacteria-targeting ligand is polymeric-based and is composed of Silane(Si)-Polyethylene glycol (PEG)-Polymyxin E(Colistin), as illustrated in FIG. 2a. The resulting blood from the output of the spiral-based fluidic apparatus is then free of disease material and is returned to the patient.

Figure 12:
FIG. 12 is a magnified illustration of a spiral-based fluidic apparatus including pillars, in accordance with an embodiment of the present invention.

In some embodiments, the fluidic device includes pillars (FIG. 12) functionalized with disease material-targeting ligands. In one embodiment, the pillars are positioned to increase the probability that the desired particles will collide and bind to the pillars, while also preventing clogging by allowing enough room for non-disease-causing material such as healthy blood cells and other materials to pass. There would be many useful patterns and arrangements that the pillars could be positioned in, and embodiments of the present invention are contemplated for use with any such arrangements.

Figure 11:
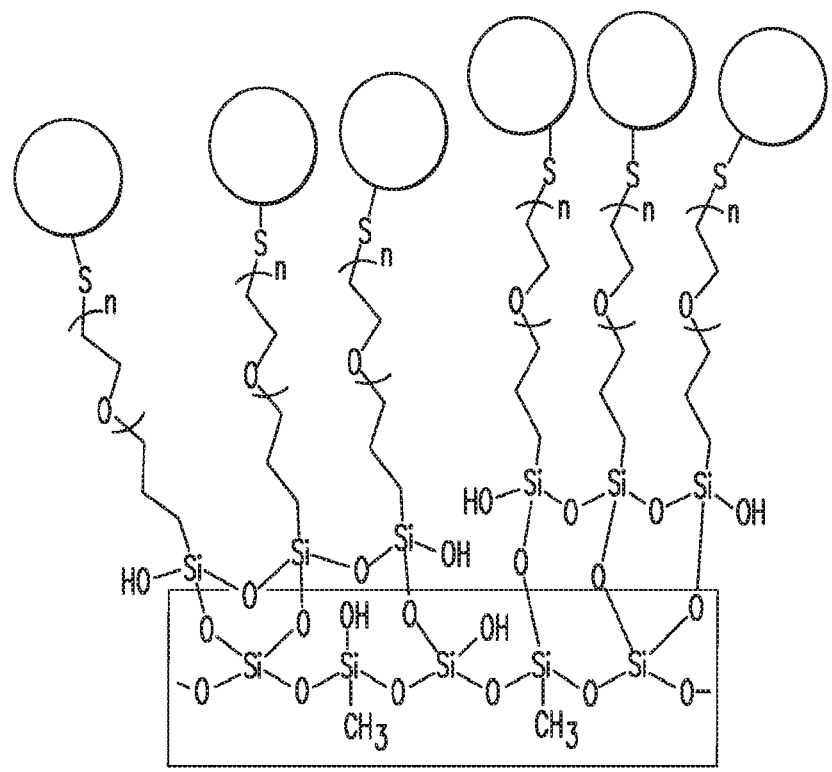
FIG. 11 is a magnified illustration of a wall of the fluidic apparatus wall composed of particles (for example, nanoparticles, microparticles, nanofiber or microfiber) functionalized with disease material-targeting ligands, in accordance with an embodiment of the present invention.

In some embodiments, the surface of the spiral-based fluidic apparatus or of the ligand (or of the pillar) is a nanoparticle or microparticle that captures cells such as bacteria (FIG. 11). A nanoparticle functionalized surface possesses nanometer scale particles functionalized with disease material targeting ligands. A microparticle surface possesses micrometer scale particles functionalized with disease material targeting ligands.

In some embodiments, following treatment, the claimed fluidic device can be used to analyze the captured disease materials via fluorescent labeling or imaging or other techniques such as cytometry. Similarly, ELISA, fluorophoric, or chromogenic reporters or substrates that generate visible color change to determine the existence of antigen or analyte may be used to analyze the sample. In some embodiments, heat may also be applied to the blood to destroy unwanted disease material. In some embodiments, medications, drugs, chemicals or any combination thereof may be employed as an adjuvant to the use of the claimed device.

In another embodiment of the present invention, the captured disease materials can be removed from the claimed device through conventional means (such as flushing its channel with buffer salt) to cleave the bond between such disease materials and the ligand. The recovered disease material may then be cultured and/or otherwise tested. This process may aid in its identification and formulation of a treatment protocol for a patient, for example. Isolation, recovery and subsequent culturing of such materials may also be used for numerous other non-patient related purposes.

In yet another embodiment of the present invention, the captured disease materials can be removed from the claimed device through conventional means (such as flushing its channel with buffer salt or lysis buffer) to cleave the bond between such disease materials and the ligand. Should the recovered disease material be bacteria, fungi or mycobacteria, the identity of the disease material could be determined by lysing the material through known means and then using either polymerase chain reaction (PCR) or matrix-assisted laser desorption/ionization time-of-flight (MALDI-TOF) on the lysed sample. This process may also aid in the speedy identification of the disease material allowing for the prompt formulation of a treatment protocol for a patient or numerous other non-patient related purposes.

Figure 7:
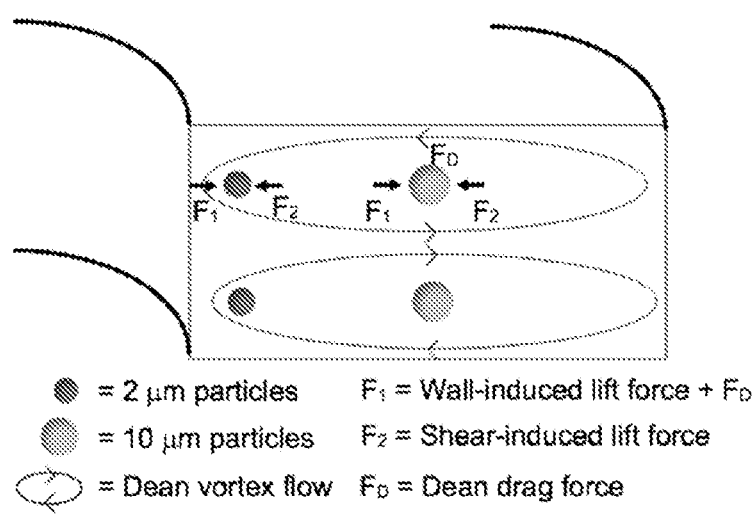
FIG. 7 is a schematic depiction of the forces within the fluidic apparatus channel Here, due to channel curvature, the two counter-rotating Dean forces are orthogonal to the main flow direction. Dean force causes recirculation of desired, healthy materials (i.e. red, blood cells) in the center of the channel. The disease material (i.e. green, disease material) are subject to inertial lift force, which focuses the targeted disease material near the ligand functionalized channel walls, as the healthy materials remain free in the channel center lumen.

In some embodiments, as shown in FIG. 7, a fluidic device that uses inertial based separation is used to separate healthy materials from disease materials in the blood. As an illustrative example, bacteria are smaller than blood cells. In some embodiments, a bacteria targeting ligand, such as Silane-Polyethylene glycol-Polymyxin E, is functionalized on the walls of the spiral-based fluidic apparatus channel or on the pillars, thereby allowing the disease material (i.e. bacteria) to be captured. As an illustrative example, bacteria are smaller than other cells in the blood such as leukocytes and red blood cells. For instance, bacteria may have diameters 0.5-2 microns, therefore a spiral can be designed to force smaller bacterial sized cells near the ligand functionalized channel walls, while allowing blood cells, which are 90% larger, to remain in the center of the channel. In some embodiments, the spiral-based fluidic apparatus is made of microfabricate material, including, but not limited to PDMS or other material like polyimide. In some embodiments, the spiral-based fluidic apparatus is made of PMMA. Bacteria are captured using specific ligands that have a high affinity for bacteria through charge based interactions.

In some embodiments of the present invention the spheres, pillars, or walls (or any combination thereof) of the claimed fluidic device are functionalized with a cationic, polymer based ligand carrying antibiotic analogues, such as Silane-Polyethylene glycol-Polymyxin E, for capturing anionic bacteria, such as *Acinetobacter baumannii*. After capture, images can be taken to further diagnose disease progression by staining with specific fluorescent antibody conjugates. Antibody targets for bacteria capture include, but are not limited to, LPS, OmpA, Lipoteichoic acid, GrfA, and Clumping Factor A.

Figure 5:
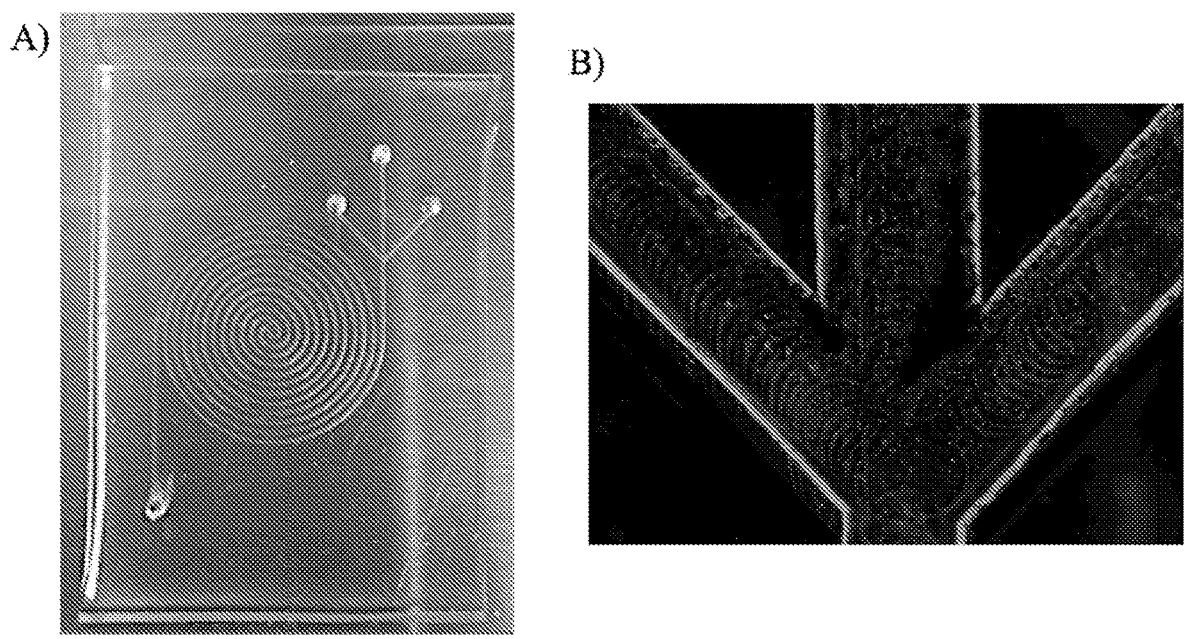
FIG. 5A illustrates a double spiral microchannel configuration useful for bacterial isolation. This configuration comprises a single inlet and three equally divided outlets.
FIG. 5B is a microscopic image illustrating the outlet section of the double spiral microchannel.

In some embodiments, the fluidic apparatus is composed of a spiral channel (FIG. 8) functionalized with disease material-targeting ligand, such as polymer-based ligands (FIG. 2a). The spiral channel is comprised of materials consisting of, but not limited to, plastic, polydimethylsiloxane (PDMS) (FIG. 5a), SU-8, polyimide, paralyne, metals, or other materials. In some embodiments, the inner surface of the spiral is modified to be receptive to the ligand, for example to a Silane-based polymeric ligand. In some embodiments, the spiral-based fluidic apparatus is functionalized with peptides. In some embodiments, the patient's blood flows through the spiral-based fluidic apparatus so that the relevant biological microorganism, cell, protein, antibody, or peptide is allowed to adhere to the ligand on the surface of the apparatus. In some embodiments, the blood may be flown back out of the spiral-based fluidic apparatus consistently at a flow rate of about 0.2 mL/min to about 200 mL/min. In alternate embodiments, the blood may be flown back out the spiral-based fluidic apparatus after a longer or shorter period depending upon the amount of time required to collect the disease material.

In some embodiments, a spiral-based fluidic apparatus with captured material (such as bacteria) (FIG. 4) are previously fluorescently labeled with fluorescent dye. For example, SYTO 9 dye is used to label the bacteria (FIG. 4) that have been captured in the spiral-based fluidic apparatus. Next, the fluorescent bacteria are quantified. In some embodiments, an automated system is used to quantitate the bacteria. Software and/or a CCD camera may be incorporated into the quantitation system to count the bacteria. In some embodiments, the bacteria within the entire apparatus is quantified. In some embodiments, bacteria within a single cross-sectional area is quantified and the total number of bacteria cells captured is extrapolated from the single bacteria count. In some embodiments, the quantification is performed following capture once the fluids are removed. There are a variety of methods used to label and quantify the cells that are captured, which are accounted for with the present invention. Also, a variety of materials can be captured and quantified, which are accounted for with the present invention.

In some embodiments, there is continuous flow through the spiral-based fluidic apparatus. In an alternate embodiment, blood is pumped through the spiral-based fluidic apparatus for a specific time period and then the flow is stopped for a specific time, then flow is resumed and the step is repeated.

In some embodiments, the capturing spiral-based fluidic apparatus is exposed to radiation to kill bacteria or other disease materials. In some embodiments, bacteria-targeting polymeric ligands are functionalized along the inner surface of the spiral-based fluidic apparatus channel. As bacteria flow through the spiral-based fluidic apparatus, they are focused near the surface of the channel that is functionalized with the disease material-targeting ligand. The bacteria then attach or/and die if ligand capturing is also used in combination with antibiotic agents. In some embodiments anti-cancer drugs, or other chemicals or drugs, are used. In some embodiments, drugs that are not necessarily cytotoxic are functionalized on the surface of the apparatus. These drugs target specific proteins expressed on cell walls that are targeted for removal, such as bacteria surface proteins or cancer cells.

In some embodiments, hyperthermia therapy may be used to aid in the removal of disease material from blood. In some embodiments, blood is pumped through the spiral-based fluidic apparatus and then heated to temperature designated to destroy or deactivate the targeted disease material. Heating the apparatus can be performed under conditions of active flow or without blood flow. In some embodiments, the spiral-based apparatus is then cooled to a medically accepted temperature. Multiple chambers, channel, or compartments can be designated and applied for heating and cooling.

In some embodiments, the inner spiral channel is functionalized with a disease material-targeting ligand, wherein the ligand is selected from the group of ligands comprising proteins, antibodies, peptides, polymers, substances that induce apoptosis, substances that bind to death receptors, tumor necrosis factors, adhesion receptors, E-selectin, and cytokines, quorum sensing protein receptors. There are various ligands that could be used that are not mentioned above.

In some embodiments, this invention may also be used to remove viruses, microorganisms, bacteria, metastatic cells, materials, cancer stem cells, peptides, proteins, enzymes, toxins, diseased cells, cancer cells, and quorum sensing proteins. In some embodiments, this invention can help reduce infections including sepsis, endocarditis, and high lactate levels. The invention may utilize biological ligands such as antibodies or peptides to capture microorganisms, bacteria, viruses, endotoxin, infectious microorganisms, cancer cells, circulating tumor cells, peptides, and other disease materials that are desired to be removed from blood.

The present disclosure also relates to the detection and capture of disease material from blood. Specifically, the disclosure relates to using a disease material targeting ligand functionalized within the fluidic apparatus described herein to capture disease material that is desired to be removed from whole blood.

In some embodiments, following flow of the blood through the fluidic apparatus, optically-active microbeads are then added to the fluidic apparatus to label disease materials captured within the channel.

In some embodiments, the microbead labeled fluidic apparatus is then optically read using an optical reader. Results are used to determine if disease materials are present in the blood and to also identify the disease material, as well as quantify the disease material load.

Figure 4:
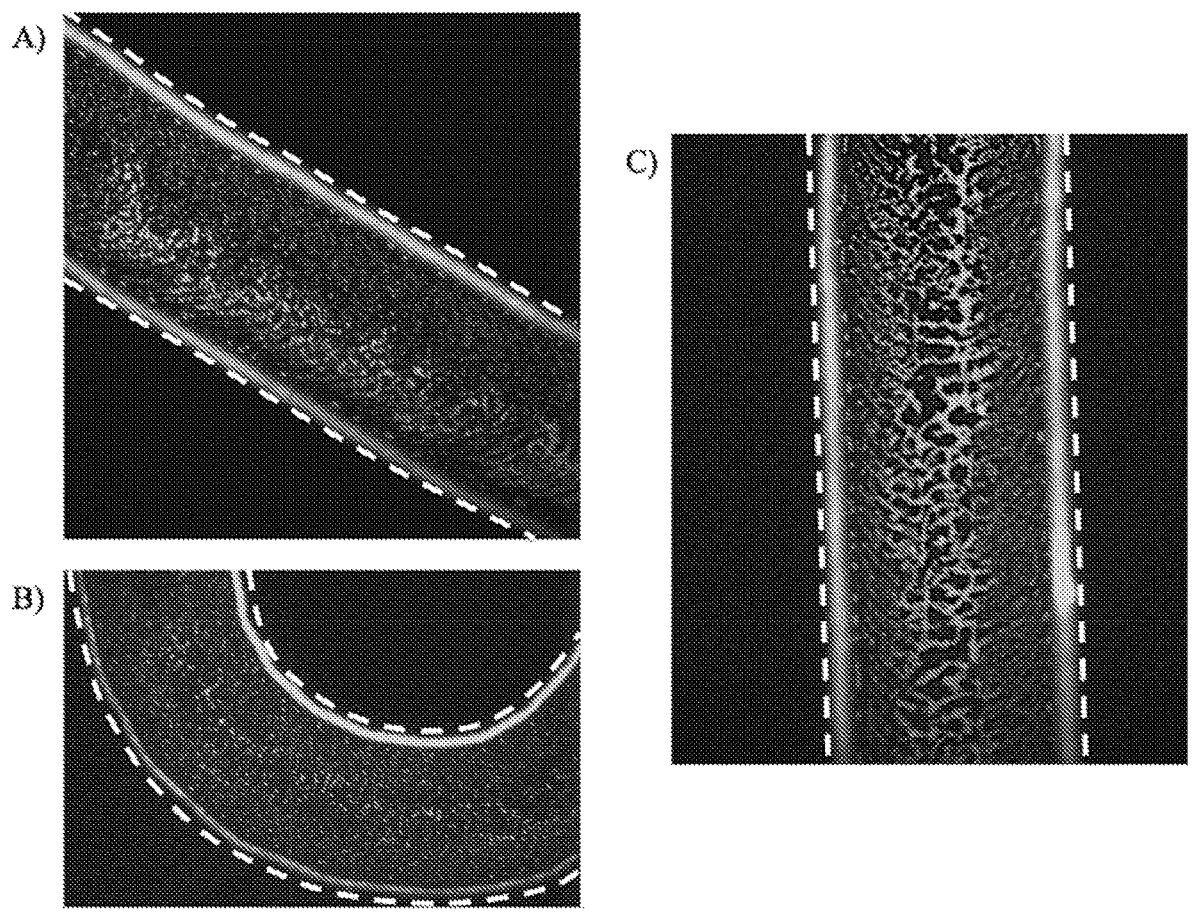
FIG. 4 shows an illustration of images indicating the isolation of bacterial cells with claimed fluidic device. Here, the bacteria (*Acinetobacter baumannii* cells fluorescently labeled) under the influence, of shear-modulated inertial forces equilibrate along the functionalized microchannel walls and bind to the ligand (Col-PEG-Si). This is evident in the specific regions shown: (A) first loop following the inlet channel, (B) center of loop, and (C) channel just prior to reaching the trifurcated outlet of the channel as the bacteria remain displaced to either side of the microchannel center (white dotted lines indicates the channel walls). The experiment was performed by flowing fluorescently labeled bacteria through the channel at a flow rate of 0.2 mL/min. The channel was then washed with diH20 four times and then imaged using fluorescent microscopy. The bacteria remained bound to the channel walls following the wash steps, as indicated by the images above.

In some embodiments, blood is flowed through a tube into the fluidic apparatus. In some embodiments, the spiral-based fluidic apparatus includes disease material-targeting ligands. In some embodiments, the ligands are antibiotics or antibodies specific to the surface markers of the disease materials that are being targeted for removal, such as bacteria. As disease material, such as bacteria, flow through the spiral-based fluidic apparatus, they are focused by inertial forces along the walls of the channel. The walls of the channel are, in this exemplary case, functionalized with a bacteria-targeting ligand (FIG. 2), thereby allowing for bacteria capture and removal (FIG. 4). In some embodiments, the bacteria-targeting ligand is polymeric-based and is composed of Silane(Si)-Polyethylene glycol(PEG)-Polymyxin E(Colistin), as demonstrated in FIG. 2. In one embodiment, the ligand, Colistin-PEG1000-Silane (Col-PEG-Si), was designed to capture bacteria. Colistin, a naturally occurring cationic decapeptide, is a potent broad-spectrum antimicrobial that is used in the clinical setting. The cationic colistin molecule and the negatively charged lipid A component of all Gram-negative pathogens interact both electrostatically and hydrophobically, allowing for Col-PEG-Si capture of bacteria. The amount of colistin conjugated to the channel surface was carefully designed to improve bacteria binding kinetics. Utilizing colistin as a targeting ligand presents many advantages over synthetic, genetically engineered, or biomacromolecular ligands that have been used in this context. One advantage is that colistin is a readily available, approved antibiotic that has been used in the clinical setting for decades. This design simplifies development and facilitates regulatory considerations relative to the use of genetically engineered or new biomacromolecular ligands. Optically-active, disease material targeting microbeads are then added to the fluidic channel. The optically-active microbeads bind to the targeted disease material. The device is then read using an optical reader.

In some embodiments, the fluidic apparatus includes pillars functionalized with disease material-targeting ligand. In some embodiments, the pillars are positioned to increase the probability that the desired particles collide and bind to the pillars, while also preventing clogging by allowing enough room for healthy blood cells and materials to pass. There would be many useful patterns and arrangements that the pillars could be positioned in, and embodiments of the present invention are contemplated for use with any such arrangement.

In some embodiments, following treatment, the fluidic apparatus can also be used to analyze the captured disease materials via ELISA, fluorophoric, or chromogenic reporters or substrates that generate visible color change to determine the existence of antigen, or analyte can be used to analyze the sample.

As an illustrative example, bacteria are smaller than blood cells. In some embodiments, a bacteria targeting ligand, such as Silane-Polyethylene glycol-Polymyxin E, is functionalized on the walls of the fluidic apparatus channel or on the pillars, thereby allowing the disease material (i.e. bacteria) to be captured. As an illustrative example, bacteria are smaller than other cells in the blood such as leukocytes and red blood cells. For instance, bacteria can have diameters of 0.5-2 microns, therefore a spiral can be designed to force smaller bacterial sized cells near the ligand functionalized channel walls, while allowing blood cells, which are 90% larger, to remain in the center of the channel. In some embodiments, the spiral-based fluidic apparatus is made of microfabricate material, including, but not limited to polymethyl methacrylate (PMMA) or other material like polyimide.

Bacteria are captured using specific ligands that have a high affinity for bacteria through charge based interactions. In some embodiments of the present invention the spheres, pillar, or walls (or any combination thereof) of the fluidic apparatus are functionalized with a polymer based ligand carrying antibiotic analogues, such as Silane-Polyethylene glycol-Polymyxin E, for capturing bacteria, such as *Acinetobacter baumannii*. After capture, images can be taken to further diagnose disease progression by staining with specific fluorescent antibody conjugates. Antibody targets for bacteria capture include, but are not limited to, LPS, OmpA, Lipoteichoic acid, GrfA, and Clumping Factor A.

Figure 2:
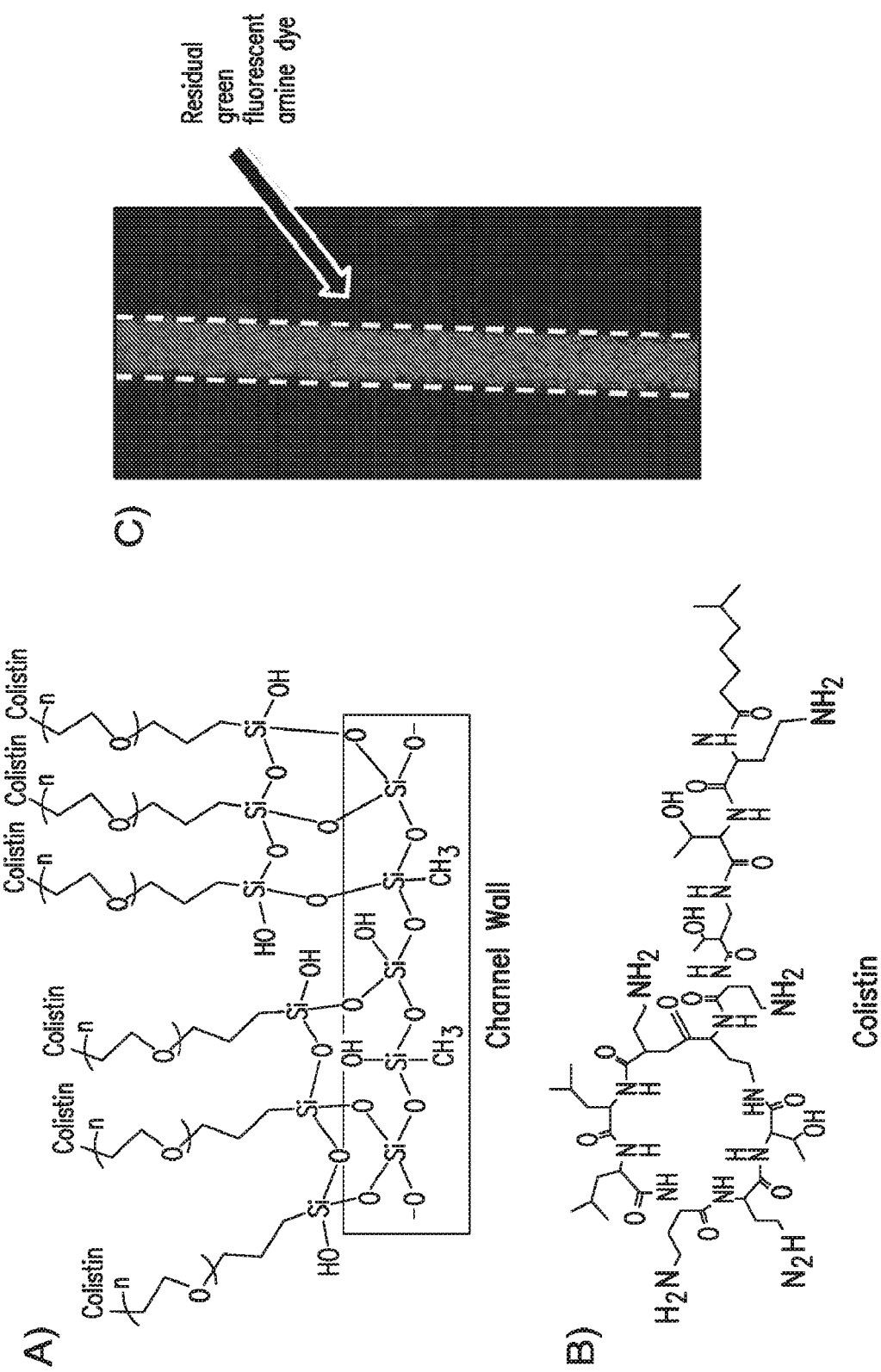
FIG. 2 illustrates the inner wall of the multidirectional channel with the ligand Colistin PEG-Silane bound thereto and its use in the capture of bacteria.

In some embodiments, the spiral-based fluidic apparatus is composed of a spiral channel (FIG. 8) functionalized with disease material-targeting ligand, such as polymer-based ligands (FIG. 2). The spiral channel is comprised of materials consisting of, but not limited to, polymethyl methacrylate (PMMA), polydimethylsiloxane (PDMS) (FIG. 5), SU-8, polyimide, paralyne, metals, or other materials. In some embodiments, the inner surface of the spiral is modified to be receptive to the ligand, for example to a Silane-based polymeric ligand. In some embodiments, the fluidic apparatus is functionalized with peptides. In some embodiments, the blood flows through the fluidic apparatus so that the relevant biological microorganism, cell, protein, antibody, or peptide is allowed to adhere to the ligand on the surface of the apparatus.

In some embodiments, a spiral-based fluidic apparatus with captured material (such as bacteria) (FIG. 4) are fluorescently labeled with optically active microbeads. For example, colistin functionalized, fluorescent microbeads can be added to the channel to label the bacteria that have been captured in the fluidic apparatus. Next, the fluorescently labeled bacteria are quantified. In some embodiments, an automated system is used to quantitate the bacteria. Software and/or a CCD camera can be incorporated into the quantitation system to count the bacteria. In some embodiments, the bacteria within the entire apparatus is quantified. In some embodiments, bacteria within a single cross-sectional area is quantified and the total number of bacteria cells captured is extrapolated from the single bacteria count. In some embodiments, the quantification is performed following capture once the fluids are removed. There are a variety of methods used to label and quantify the cells that are captured, which are accounted for with the present invention. Also, a variety of materials can be captured and quantified, which are accounted for with the present invention.

Use as a treatment modality in sepsis demands both increased flow capacity to accommodate the blood volume of larger living systems and a way to isolate Gram-positive bacteria. Disclosed herein is a method for scale-up using the same quantitative approach and design principles applied to the original device (FIG. 8; FIG. 26). *A. baumannii* capture occurs with equal effectiveness after increasing the cross-sectional area of the fluidic device while holding the volume to surface area ratio constant. Importantly, this is also done to include devices possessing capture agents for Gram-positive bacteria. Combination devices offer the capability to remove bacteria regardless of presentation as Gram-positive, Gram-negative, or antibiotic resistant, thus enabling early treatment in the absence of positive bacterial culture or strain identification from a blood sample. Furthermore, the simultaneous removal of bacteria and endotoxin offers a powerful, previously untested approach for the treatment of sepsis. This work highlights the transformative impact that is achieved through expanded application of biomedical engineering principles to the treatment of biological fluids and blood infections, of which sepsis is only one example. Other similarly challenging disorders, such as endocarditis, can also benefit from a similar approach.

EXAMPLES

The following examples are set forth below to illustrate the devices, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Figure 3:
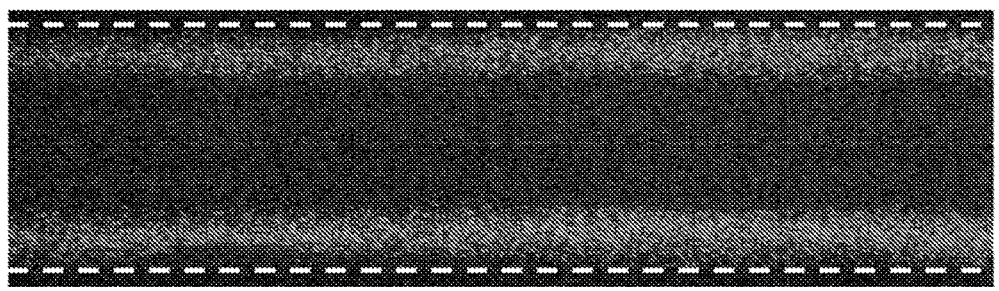
FIG. 3 illustrates a microchannel aspect ratio (AR) which promotes 2 μm polystyrene particle focusing. This particle size is comparable to the size of most bacterial cells. The averaged composite images illustrate 2 μm particle equilibration at a flow rate of 0.2 mL/min is displayed. The microchannel dimensions are congruent across the entire length of the channel, consisting of a 254 μm width by 15 μm height. The schematic indicates the approximate position of the 2 μm polystyrene particles within the microchannel cross-section just prior to reaching a trifurcated outlet (dotted lines indicate approximate position of channel walls).

Example 1. Antibiotic Functionalized Microfluidic Device for Bacterial Capture and Removal In the present example, a device and a method for isolating bacteria from flowing fluid has been developed. A bacteria-contaminated sample was introduced into at least one inlet of a microfluidic device comprised of one or more channels (FIGS. 1A and 1B). The channel walls were continuously functionalized with the biocompatible ligand, Colistin-PEG 1000-Silane (Col-PEG-Si) (FIGS. 2A, 2B, and 2C) that specifically bound to and captured bacteria from flowing fluid with a high affinity. Each channel had an aspect ratio and curvature designed to leverage inertial forces, which forced bacterial cells and bacterial sized particles along the walls of the microchannel (FIG. 3). This lead to capture of bacteria along the functionalized channel walls (FIGS. 4A, 4B, and 4C). All other cell types, including blood cells, were not captured by the bacterial-targeting ligand and freely flowed along a second portion of the channel. This resulted in non-contaminated fluid leaving through the channel outlet(s). Colistin surface presentation within the microchannel was characterized, and the results demonstrated the rapid binding of bacteria to the Col-PEG-Si.

In this example, the novel colistin-functionalized microfluidic device is comprised of materials with proven in vivo safety and efficacy. This allowed the blood-borne subset of pathogens to be removed and eradicated from the infected system, possibly reducing the spread of bacteria to distal sites. Selective removal of circulating bacteria from the bloodstream aids in rebalancing the innate immune system, thereby, leading to a decrease in inflammatory mediator levels, improvement of vascular function, and enhanced hemodynamics. The device also eliminated the need for integration of complex external force fields, such as magnets, making the device easy to operate. The device did not require nanoparticles and was composed entirely of materials that are FDA approved and biocompatible, avoiding negative side effects such as nanoparticle accumulation in organs. The system has a high processing throughput and is capable of high flow rates, making it suitable for processing an infected patient's blood in an impactful timeframe. Results show that the spiral microfluidic device of the present example overcomes the problems associated with clogging and induced cell deformation. Furthermore, the device can help to counter antibiotic ineffectiveness and overuse, subsequently reducing the threat of multi-drug resistant bacteria.

Example 2. Inertial-Based Fluidic Platform for Rapid Detection and Capture of Blood-Borne Pathogens Extracorporeal extraction of pathogens and endotoxins using inertial-based fluidics can be used as a next-generation technology to reduce sepsis-associated morbidity and mortality.

Synthesis of Colistin-PEG-Silane Ligand

NHS-PEG-Silane (N-Hydroxysuccinimide-Polyethylene glycol$_{1000}$-Silane, Nanocs, Inc., Lot #160429) (30 mg mL$^{-1}$) was dissolved in ethanol/water, pH 5 (50/50 v/v %, pH adjusted with acetic acid). 35 mg mL$^{-1}$ of colistin sulfate (Sigma-Aldrich, Lot #SLBN5158V) was added to the NHS-PEG-Silane solution. The solution was vortexed for 30 seconds and then allowed to react at 21° C. for 2 h. NHS was used to couple a heterobifunctional NHS-PEG-Silane linker to one of the five similarly reactive L-α-diaminobutyric acid (Dab) residues of colistin, resulting in Colistin-PEG-Silane.

PEG-Silane Ligand Solution Preparation

PEG-Silane (Polyethylene glycol$_{1000}$-Silane, Nanocs, Inc., Lot #1607060H) (30 mg mL$^{-1}$) was dissolved in ethanol/water, pH 5 (50/50 v/v %, pH adjusted with acetic acid). The solution was vortexed for 30 seconds and then allowed to incubate at 21° C. for 2 hours.

Design and Fabrication of Device

The microfluidic device pattern was designed and drawn in AutoCAD software (AutoCAD 2014, AutoDesk, Inc.). The design consisted of a 6-loop double spiral microchannel with one inlet and one outlet. The microchannel rotates clockwise for 6 loops, changes direction through the S-junction, then rotates counterclockwise to form the double spiral. The double spiral microchannel has dimensions of 406 mm L, 300 μm W, and 15 μm H. The spacing between two adjacent loops is 500 μm. The outermost radius of curvature is 9.8 mm. Standard photolithographic techniques were used to generate a mold from a silicon master that was spin coated with a SUS-2010 (MicroChem Corp.) layer (WS-400 Lite Series Spin Processor, Laurell Technologies Corp.) on a 4-inch silicon wafer (Nova Electronic Materials). After soft baking at 95° C. for 5 minutes, the SU-8 layer was patterned using a mask aligner (MJB 3 Mask Aligner, Suss Micro-Tech) with a UV light (Novacure 2100, Exfo Inc.) and a negative photomask (Infinite Graphics. Inc.). After subsequent post-exposure bake steps at 95° C. for 5 min, the resulting wafer was developed using SU-8 developer (MicroChem Corp.). A final hard bake was performed for 5 min at 150° C. The wafer was used as the master mold to cast the microfluidic channels. Degassed PDMS (polydimethylsiloxane, mixed in a 10:1 ratio of PDMS base with curing agent, Sylgard 184, Dow Corning Inc.) was cast over the mold and baked at 65° C. for 4 h. The PDMS with embedded channels was subsequently cut by razor blade and removed from the master mold. One inlet and one outlet were punched through the PDMS using a 1.5 mm biopsy punch (Integra Miltex). The PDMS slab was then bonded to a glass substrate (43 mm×50 mm, Ted Pella, Inc.) post oxygen plasma treatment (PDC-001 Plasma Cleaner, Harrick Plasma). Immediately following plasma treatment and bonding to the glass cover slip, 1/16" O.D. tygon microbore tubing (Cole Painter Corp.) was inserted through both the inlet port and outlet port. Colistin was tethered to the double spiral microfluidic device channel walls using the Colistin-PEG-Silane linker and silane chemistry (FIG. 19). Colistin-PEG-Silane solution was flowed through the oxidized PDMS microchannel using a 1 mL luer-lock disposable syringe (Becton Dickinson). The Colistin-PEG-Silane solution was allowed to contact the microchannel surface for 30 min at 65° C., according to well established silanization principals. Use of the heterobifunctional Colistin-PEG-Silane linker was designed to enable colistin decoration of the microchannel walls with a PEG molecular spacer, which was intended to reduce steric hindrance of colistin interactions with bacteria and endotoxin. In the range of physiological pH values, the primary amine groups of colistin are protonated, and, therefore, positively charged. The positive charge of colistin allows for binding to the negatively charged outer membrane of Gram-negative pathogens and endotoxin. PEG-Silane functionalized devices were also synthesized using a very similar approach, and used as a PEGylated control group that lacked colistin decoration. No ligand was added to result in non-functionalized double spiral microfluidic devices.

Confirmation of Colistin Conjugation to Microchannel Walls

Fluorescent labeling of colistin within the colistinated double spiral microfluidic device was performed using ATTO 488 NHS ester (Sigma-Aldrich, Lot #BCBQ4012V). ATTO 488 NHS ester (2 mg mL$^{-1}$) was dissolved in dimethylsulfoxide (DMSO, Sigma-Aldrich) immediately prior to use. Labeling was carried out by adding the fluor to the colistinated microchannel, followed by incubation for 30 minutes at room temperature. The stained microchannel was then washed with phosphate buffer saline (PBS, Gibco, Lot #1806048), pH 7.4. The same protocol was used on the PEGylated microchannel as a control. The fluorescently stained microchannels were then imaged using a fluorescent microscope (EVOS FL, Invitrogen). Image-J software was used to quantitate the fluorescent intensity across the channel width of captured images. Dilutions of ATTO 488 NHS ester within non-functionalized microfluidic devices were used as references to generate an ATTO 488 NHS ester standard fluorescence calibration curve. The fluorescence intensity of the colistinated microchannel and the PEGylated microchannel were compared to that of the ATTO 488 NHS ester standard curve, which allowed for quantification of the number of colistin molecules per double spiral microchannel.

Colistin Retention

The possibility of Colistin-PEG-Silane ligand disassembly from the surface of the double spiral microfluidic device under flow conditions was evaluated using MaxSignal® Colistin enzyme-linked immunosorbent assay (ELISA) test kit (BIOO Scientific, Lot #109501081415$626311708249). PBS, pH 7.4, was flowed through the colistinated double spiral microfluidic device at 0.2 mL min$^{-1}$ for 2 h. Sample was collected from the device outlet at various time points (1, 2, 4, 5, 10, 20, 30, 45, 60, 120 minutes) for analysis. Total colistin content in each sample was quantified by the colistin ELISA according to the manufacturer's instructions. Absorbance was measured at 450 nm using a microtiter plate reader, and these values were used to calculate the colistin concentration in the samples according to the calibration curve (assay detection range, 0.5 to 50 ng/ml). Results from colistin ligand retention characterization prompted the washing of each double spiral microfluidic device continuously for 30 minutes with 70% ethanol prior to experimental use, resulting in negligible colistin release during the capture studies.

Microbial Culture

Bacterial cultures (i.e., *Acinetobacter baumannii* ATCC17978 Colistin-resistant *Acinetobacter baumannii* 19606R[41], Colistin-resistant *Acinetobacter baumannii* 'Patient 2'. *Klebsiella pneumoniae* ATCC700603. *Bacillus subtilis* 1A578 (*Bacillus* Genetic Stock Center), *Staphylococcus aureus* ATCC29213) were plated on LB agar (Sigma-Aldrich, Lot #SLBR1403V) and grown overnight at 37° C. Single colonies of each strain were then inoculated in LB broth (1×) (Gibco, Lot #1803272) and grown at 37° C. for 18 hours shaking at 150 rpm. Cell concentrations were measured with OD595 spectrometry (Infinite F500, Tecan).

Inertial Focusing Visualization

Polystyrene microspheres (Spherotech Inc.) with mean diameters of 10.2 μm±4 μm and 2 μm±0.3 μm were used to analyze particle focusing within the microchannel. Suspensions were provided at 1% w/v with 1 vol % of Tween-20 surfactant (Sigma-Aldrich) to prevent particle aggregation.

Equal volumes of two suspensions were diluted to 0.1% w/v using de-ionized (DI) water. The fluorescent particles were individually introduced into the non-functionalized double spiral microchannel at 0.2 mL min$^{-1}$ using an infusion syringe pump (Nexus 3000, Chemyx Inc.) connected to the input port of the microchannel through a 1 mL luer-lock tip syringe and 1/16" O.D. tygon inlet tubing. Particle trajectories and focusing within the double spiral channel were visualized in real-time using fluorescence microscopy (EVOS FL, Invitrogen). This process was repeated using SYTO®9 green fluorescent nucleic acid labeled (5 mM solution in DMSO, Molecular Probes, Lot #1687876A) *A. baumannii* ATCC17978. After a 5-minute incubation with SYTO®9, the bacteria were washed three times with RNase-free, ultrapure water (USB Corp., Lot #4235512) and resuspended to a concentration of ~$10^7$ colony forming units (CFUs) mL$^{-1}$. The fluorescently labeled bacteria suspension was flowed through a PEGylated double spiral microfluidic device at 0.2 mL min$^{-1}$ using an infusion syringe pump. Bacterial trajectories and focusing within the double spiral channel were visualized in real-time using fluorescence microscopy (EVOS FL, Invitrogen).

Susceptibility Testing

Colistin minimum inhibitory concentrations (MIC) of bacterial strains were confirmed by standard agar dilution methods. Results were interpreted according to the Clinical and Laboratory Standards Institute susceptibility breakpoints.

Bacterial Capture Visualization

*A. baumannii* ATCC17978 was labeled with SYTO®9 as previously described in the 'inertial focusing visualization' methods section. The fluorescently labeled bacteria suspension was flowed through the colistinated and PEGylated double spiral microfluidic devices at 0.2 mL min$^{-1}$ using an infusion syringe pump. The devices were then washed four times with PBS, pH 7.4, to remove any weakly bound bacteria. Fluorescent images of the microchannels were obtained using fluorescence microscopy (EVOS FL, Invitrogen). This process was repeated using fluorescently labeled *A. baumannii* ATCC17978 and *S. aureus* ATCC29213 spiked into EDTA-anticoagulated, whole human blood. Human blood was obtained from healthy donors with informed consent in accordance with the Vanderbilt University Human Subjects Institutional Review Board (IRB) (protocol number 111251).

Bacterial Capture Quantification

Testing of the pathogen-capture capacity of the colistinated and PEGylated double spiral microfluidic devices were carried out by first adjusting an *A. baumannii* ATCC17978 bacterial suspension to ~$8 \times 10^7$ CFUs mL$^{-1}$ in PBS. pH 7.4. A concentration of ~$10^2$ CFUs mL$^{-1}$ was obtained by serial dilution of the initial suspension, which served as the control, Bacterial samples were infused through the colistinated double spiral microfluidic device at 0.2 ml min$^{-1}$, and samples were collected from the device outlet at 5 different time points (1, 2, 3, 4 and 5 minutes). This process was also repeated for the PEGylated double spiral microfluidic device. The recovered solutions from the outlet of the double spiral microfluidic devices were diluted in the same fashion as the control group. The collected samples and control were plated on LB-agar Petri dishes in triplicate (100 µL) for quantitating pathogen-capture capacity. Plates were incubated at 37° C. for 24 h, and colonies formed on the Petri dishes were counted. The number of the initial and recovered bacteria were calculated by multiplying the average number of colonies counted from the replicates by their respective dilution factor. The number of captured bacteria was determined by subtracting the number of recovered bacteria from the initial amount of bacteria (i.e. untreated control group). The capture capacity was calculated by dividing the number of captured cells by the number of initial cells. Capture capacity of the following bacterial strains in PBS, pH 7.4 was quantified: *A. baumannii* ATCC17978, colistin-resistant *A. baumannii* 19606R, colistin-resistant *A. baumannii* 'Patient 2', *K. pneumoniae* ATCC700603, and *B. subtilis* 1A578. This process was also repeated for *A. baumannii* ATCC17978 spiked into EDTA-anticoagulated, whole human blood.

Endotoxin Binding Assay

The Pierce LAL Chromogenic Endotoxin Quantification kit (Thermo Scientific, Lot #RG236327) was used according to the manufacturer's protocol to quantify the endotoxin capture capacity of the colistinated and PEGylated double spiral microfluidic devices, respectively. Briefly, *Escherichia coli* (*E. coli*) Endotoxin Standard (011:B4) was reconstituted in endotoxin-free water at a concentration of 1 EU mL$^{-1}$ (Endotoxin Unit) and the solution was flowed through the colistinated double spiral microfluidic device at 0.2 ml min$^{-1}$ using an infusion syringe pump. Samples were collected from the device outlet at 5 different time points (1, 2, 3, 4 and 5 minutes). This process was repeated for the PEGylated double spiral fluidic device. Collected samples were then analyzed for endotoxin concentration according to the manufacturer's protocol, and results were read at 450 inn.

Hematology Studies

To determine whether treatment with the double spiral microfluidic device significantly changes blood hematologic parameters. 1 mL of EDTA-anticoagulated whole, human blood was collected from the colistinated device outlet after being flowed through the blood-cleansing device at 0.2 ml min$^{-1}$. This process was repeated for the PEGylated device. Red blood cell lysis was then analyzed to determine release of free hemoglobin in plasma. Plasma hemoglobin was measured by according to well-established protocols. Following passage through the device, the blood samples were centrifuged (500×g) and the supernatant was spectrophotometrically analyzed for hemoglobin release using a plate-reader (Tecan, Infinite M1000 Pro) at 451 nm in order to determine percent hemolysis relative to the Triton-X positive control. Triton X-100 (Sigma-Aldrich) was diluted in diH2O to result in a 20 v/v % Triton-X detergent concentration, which served as the positive control. The negative control used was EDTA-anticoagulated whole, human blood that was not flowed through a double spiral microfluidic device (i.e. untreated). Percent of hemoglobin release was calculated according to the following equation: Hemoglobin release (%)=[(Sample$_{451nm}$−Negative control$_{451nm}$)/(Positive control$_{451nm}$−Negative control$_{451nm}$)]×100%. Complete blood counts of each sample (i.e. untreated, colistinated device, PEGylated device) were performed by the Vanderbilt University Translational Pathology Shared Resource Core.

Device Scale-Up

A larger version of the initial double spiral microfluidic device was fabricated and functionalized using the previously described methods. The scaled-up version of the device consisted of a 4-loop double spiral microchannel with one inlet and one outlet, Dimensions of the scaled-up version were 323 mm L, 750 µm W, and 15 µm H. The spacing between two adjacent loops was 500 µm and the radius of the outermost curvature was 11.2 mm. The dimensions of the scaled-up device were adjusted such that the volume to surface area ratio was comparable to that of the initial device design. The bacterial capture capacity of the scaled-up device was characterized to compare the capture capacity to that of the smaller device. The 'bacterial capture quantification' assay using the scaled-up device was performed with *A. baumannii* ATCC 17978.

Statistical Analysis

All measured values are reported as an average mean of at least triplicate samples±standard deviation (SD), as indicated by error bars. Significant differences were determined using a one-way ANOVA followed by post hoc Tukey's multiple comparison test, as defined by P values<0.01.

Results

Colistin Conjugation to Microchannel Walls

Fluorescent labeling and stoichiometric analysis were used to estimate that 1.76 µg of colistin was functionalized along the walls of the colistinated double spiral device (FIG. 20). The amount of colistin associated with the surface of this device is non-toxic to humans. An ELISA was performed to estimate the amount of colistin-containing molecules that were released from the double spiral microfluidic device. Continuous flow for 2 hours resulted in approximately 300 ng of colistin release from the channel (FIG. 21).

Inertial Particle Focusing in the Double Spiral Microfluidic Device

Fluorescent polystyrene microparticles under continuous flow conditions were imaged within the non-functionalized double spiral microfluidic channel. At a volumetric flow rate of 0.2 ml min$^{-1}$, with corresponding Re=14.9, 2 µm sized particles were focused near the inner wall of the microchannel (FIG. 14a), while 10.2 µm size particles were focused near the center of the microchannel width (FIG. 14b). The composite fluorescence images showed the trajectories of the 10.2 µm (red stream) and 2 µm particles (green stream), with the larger particles approximating the trajectory of larger blood cells (i.e. red blood cells and white blood cells). Microparticles were inertially focused at equilibrium positions as a function of diameter. A clear separation of bacterial-sized particles from blood cell-sized particles was evident. *A. baumannii* ATCC17978 were inertially focused even closer to the channel wall than 2 µm diameter spherical particles. In addition, bacteria appeared near both lateral surfaces of the double spiral device. These behaviors were in agreement with the inertial design as derived from net inertial lift force ($F_L$) and Dean drag force ($F_D$).

Bacterial Cell Capture Using Surface-Modified Double Spiral Microfluidic Device

*A. baumannii* ATCC17978 bacterial cells were chosen as the standard specimen for qualitatively and quantitatively evaluating the bacterial capture capacity of the colistinated and PEGylated double spiral microfluidic devices. Green, fluorescently labeled *A. baumannii* ATCC17978 were bound to the colistinated microchannel walls following passage through the microfluidic device at 0.2 mL min$^{-1}$ and subsequent washing (FIG. 4). Significant bacterial capture did not occur within the PEGylated double spiral microfluidic device, presumably due to the absence of colistin surface functionalization (FIG. 4).

Bacterial capture capacity was quantified by flowing 1 mL of *A. baumannii* ATCC17978 suspension in PBS, pH 7.4, through the microfluidic devices at a flow rate of 0.2 mL min$^{-1}$. A bacterial cell capture capacity of over 10$^7$ CFUs was achieved with a single passage through the colistinated double spiral microfluidic device (FIG. 15a), as confirmed by the reduction of colonies that could be cultured from the fluid exiting the device. *K. pneumoniae* ATCC700603, another Gram-negative human pathogen, was also successfully removed from flowing fluid (FIG. 15b). The colistinated double spiral microfluidic device also captured and removed antibiotic-resistant organisms, including colistin-resistant *A. baumannii* 'Patient 2' and colistin-resistant *A. baumannii* 19606R, from flowing fluid (FIGS. 15c and 15d). These colistin-resistant strains are well characterized in literature and colistin-resistance was reconfirmed through MIC assessment (Table 1).

TABLE 1

Colistin resistance.

| Sample | Colistin MIC (µg/mL) |
| --- | --- |
| *Acinetobacter baumannii* 19606R[40] | >256 |
| *Acinetobacter baumannii* 'Patient 2'[41] | >256 |

Minimum inhibitory concentrations (MICs; µg/ml) of colistin-resistant *A. baumannii* isolates.
Results are listed as the mean ± SD, n = 3.

Binding of green fluorescent *A. baumannii* ATCC17978 to the colistinated double spiral microchannel device was strongly supported by PEG functionalization (FIGS. 15a-15d). Colistinated and PEGylated devices did not capture Gram-positive *B. subtilis* 1A578, confirming specificity for Gram-negative pathogens in colistin-functionalized devices (FIG. 22).

Extracorporeal Blood Cleansing

The blood-cleansing capability of the double spiral microfluidic device was assessed using fresh, whole human blood that was EDTA-anticoagulated and experimentally contaminated with *A. baumannii* ATCC17978. A single colistinated double spiral microfluidic device removed approximately 10$^7$ colony forming units of bacteria from whole blood with one pass through the device at a flow rate of 0.2 ml min$^{-1}$ (FIG. 16a). Bacterial cell capture from flowing blood was also confirmed using fluorescence microscopy. Green, fluorescently labeled *A. baumannii* ATCC17978 is bound to the colistinated microchannel walls following passage of infected blood through the microfluidic device at 0.2 mL min$^{-1}$ and subsequent washing (FIGS. 16b and 16c). Gram-positive *S. aureus* ATCC29213 spiked in whole, human blood, however, did not bind to the colistinated microchannel walls, confirming specificity for Gram-negative pathogens in the colistin-functionalized devices (FIG. 16d). Flowing whole, human blood through the colistinated and PEGylated double spiral microfluidic devices had no detectable effect on blood composition (Table 2), nor did it induce red blood cell hemolysis (Table 3).

TABLE 2

Blood cell counts of whole, human blood before and after passage through functionalized microfluidic devices.

| Sample | Red blood cells (trillion cells/L) | White blood cells (billion cells/L) | Platelet (billion cells/L) |
| --- | --- | --- | --- |
| Control | 4.60 ± 0.70 | 6.80 ± 0.30 | 239 ± 26.6 |
| Colistinated device | 5.00 ± 0.10 | 7.30 ± 0.30 | 236 ± 0.90 |
| PEGylated device | 5.10 ± 0.10 | 6.50 ± 0.90 | 273 ± 84.3 |

Red blood cell counts, white blood cell counts, and platelet counts of blood flowed through colistinated and PEGylated double spiral fluidic devices at 0.2 mL min$^{-1}$ were not significantly different than the control group. Unaltered blood not passed through a microfluidic device was used as the control. Data were compared using one-way ANOVA followed by post hoc Tukey's multiple comparison test. Results are listed as the mean±SD, n=3. *P<0.01 P<0.001 *P<0.0001.

TABLE 3

Summary of hemolysis levels of whole, human blood flowed through functionalized microfluidic devices.

| Sample | Hemolysis (%) | Statistical Significance |
|---|---|---|
| Positive control (20 v/v % Triton-X) | 100% ± 3.08% | *** |
| Negative control | 0.01% ± 0.70% | control |
| Colistinated device | 1.09% ± 1.09% | n.d. |
| PEGylated device | 1.86% ± 0.66% | n.d. |

Whole, human blood was flowed through the colistinated and PEGylated double spiral microfluidic devices. Blood passage through the devices did not cause hemolysis. Blood containing Triton-X (20 v/v %) was used as a positive control. The negative control was blood that was not passed through a double spiral fluidic device. Data were compared using one-way ANOVA followed by post hoc Tukey's multiple comparison test. Results are listed as the mean±SD, n=5. *P<0.01, P<0.001, *P<0.0001.

Total Bacterial Capture Capacity

The colistinated double spiral microfluidic device removed ~$10^7$ CFUs of live *A. baumannii* ATCC17978 (FIG. 1.5$a$) and a similar quantity of *K. pneumoniae* ATCC700603 (FIG. 15$b$) from PBS within 5 minutes of device operation. In addition, colistin-resistant strains of *A. baumannii* (i.e. *A. baumannii* 19606R and *A. baumannii* 'Patient 2') were captured with equal efficacy as the wild-type, colistin sensitive *A. baumannii* strain (FIG. 17). Statistical analysis confirmed that the colistinated double spiral microfluidic device captured Gram-negative bacteria from whole, human blood at a capacity that is not significantly different than in PBS (FIG. 17).

Quantification of Endotoxin Capture

Endotoxin, one of the principal components of the outer membrane of Gram-negative bacteria, also contributes to the systemic inflammatory response that is characteristic of sepsis. Therefore, the removal of endotoxin from flowing fluid using the double spiral microfluidic device was assessed. Endotoxin was spiked into endotoxin-free water and continuously flowed through the device at 0.2 mL min$^{-1}$ for 5 minutes, totaling 1 mL. Endotoxin was rapidly captured from the fluid passing through the colistinated double spiral microfluidic device, with endotoxin capture efficiency approaching 100% in single pass operation (FIG. 23). In contrast, endotoxin was not effectively captured using the PEGylated device, demonstrating the critical requirement for colistin in endotoxin retention in the double spiral.

Device Scale-Up for Clinical Translation

Figure 8:
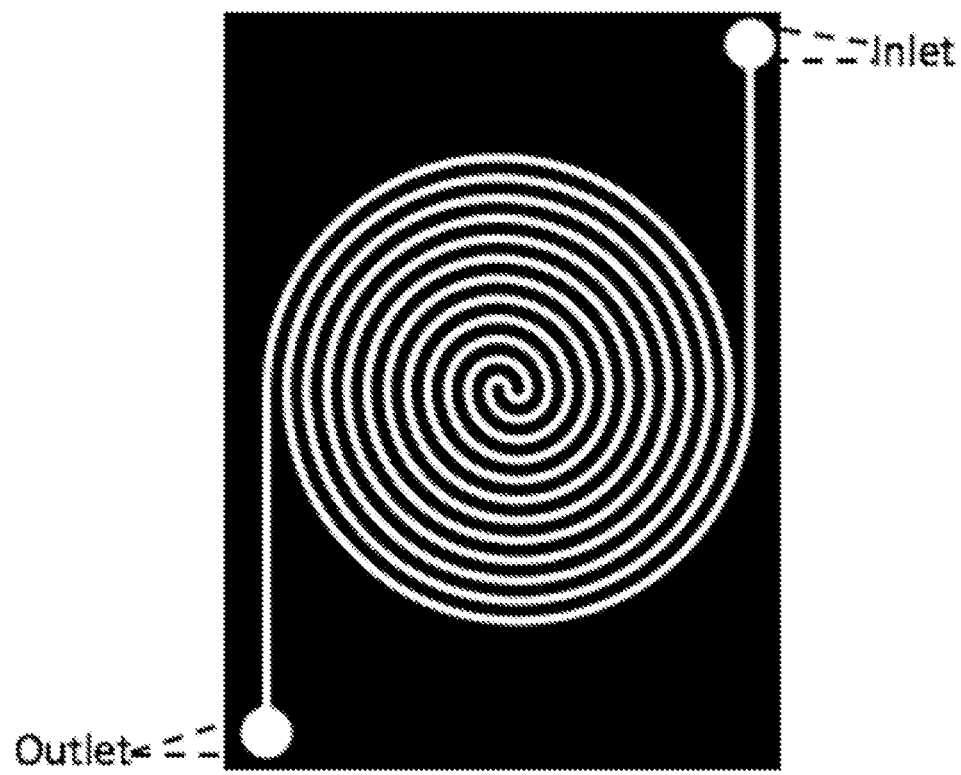
FIG. 8 is a further illustration of a spiral-shaped fluidic apparatus designed to target and capture disease material, in accordance with an embodiment of the present invention.
Figure 9:
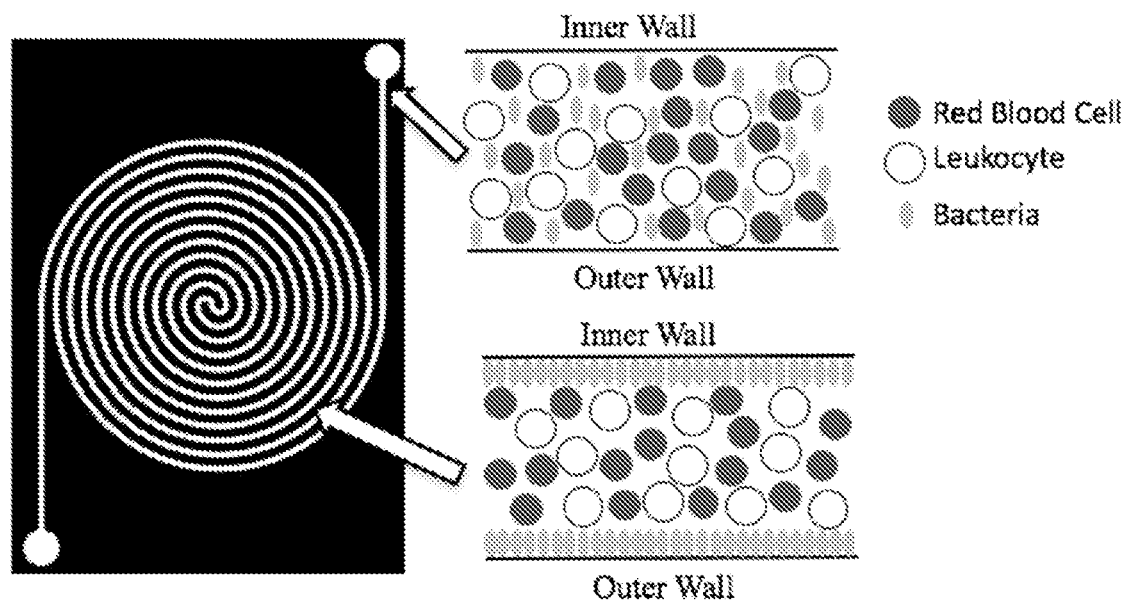
FIG. 9 is another illustration of a spiral-shaped fluidic apparatus that depicts how inertial forces focus target disease material, in this case bacteria, near the ligand functionalized channel walls, as the healthy materials (i.e. blood cells) remain free in the channel center lumen.
Figure 10:
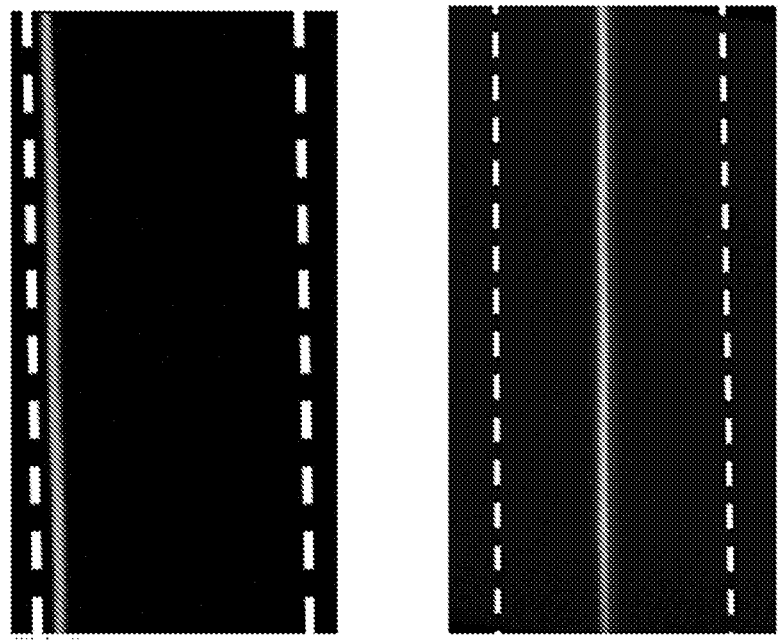
FIG. 10 is an image taken using a fluorescent microscope that captures the focusing of disease material (left) near the walls in a spiral-based fluidic device within the scope of the present invention. Healthy material (right) remains within the center of the spiral-based fluidic apparatus channel under flow conditions.

The capture capacity of the described colistinated double spiral microfluidic device is approximately $10^7$ CFUs (FIG. 17), which exceeds the requirements to treat a septic patient by more than three orders of magnitude. However, for potential clinical translation, the flow rate associated with the current device design must be increased to enable treatment of larger animal models and humans. Therefore, a larger version of the double spiral fluidic design was developed to demonstrate the feasibility of scaling up the current design. The scaled-up version of the colistinated double spiral microfluidic device, operating at a flow rate three times greater than that used with the initial design, captured of over $10^7$ *A. baumannii* ATTC17978 CFUs in single pass operation (FIG. 8). Dimensions of the scaled-up device were selected to provide a volume to surface area ratio similar to that of the original device, while maintaining appropriate hydrodynamic particle focusing characteristics. The governing principles of fluid transport in closed conduits can be used to design a larger double spiral device with performance characteristics appropriate for increased treatment volumes.

Figure 15:
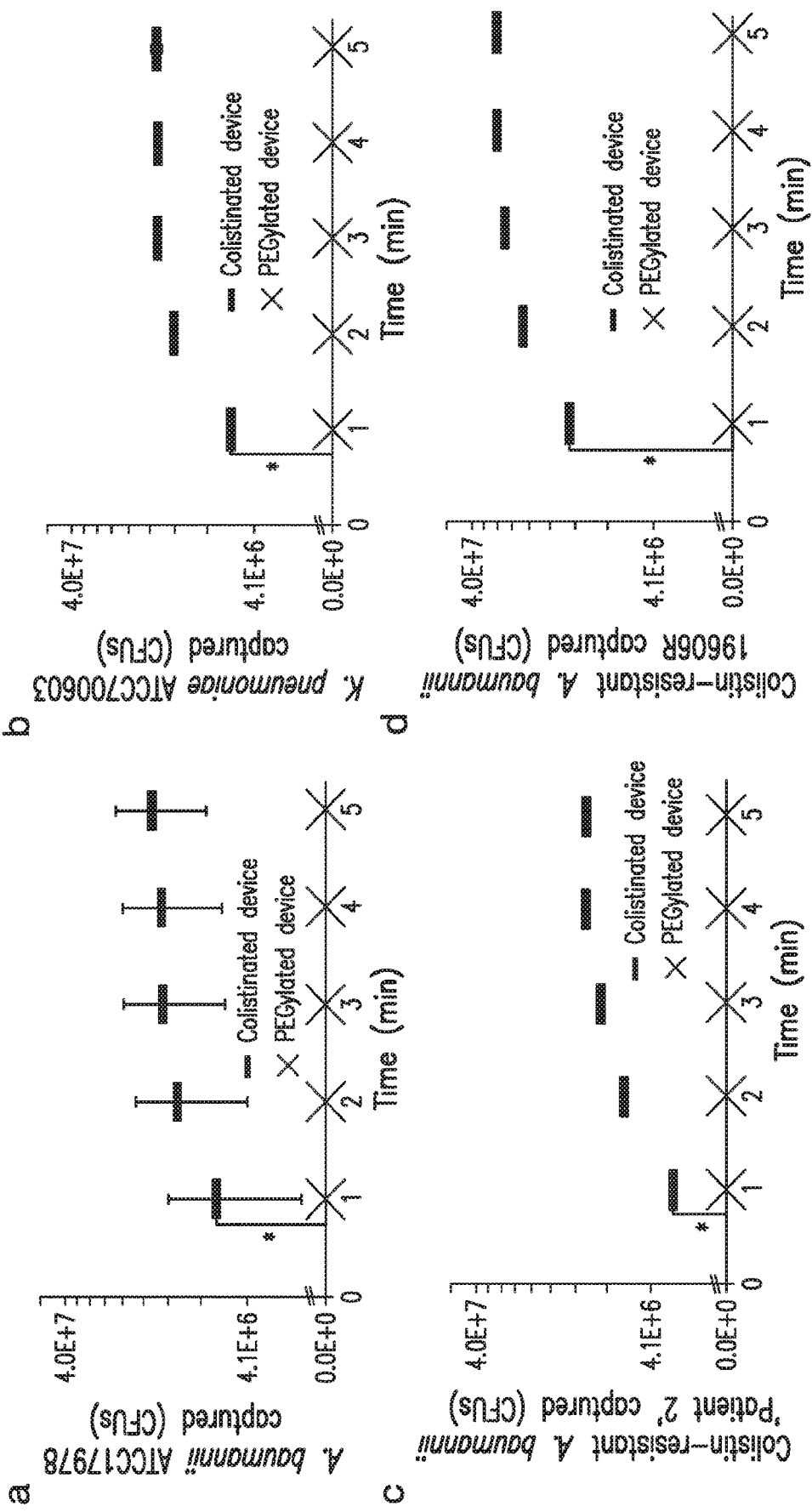
FIG. 15 illustrates an example of the quantification of bacterial capture capacity of one configuration of an embodiment of the claimed device. Pathogen capture capacity of Gram-negative bacterial isolates when spiked into PBS and flowed through a colistinated and PEGylated double spiral microfluidic devices at 0.2 ml min$^{-1}$. a, *A. baumannii* ATCC17978. b, *K. pneumoniae* ATCC700603. c, Colistin-resistant *A. baumannii* 'Patient 2'. d, Colistin-resistant *A. baumannii* 19606R. Results are plotted as the mean±SD, n=3. *P<0.01.

The requirement for colistin functionalization suggests that wild-type *A. baumannii* capture is mediated by colistin (FIG. 4, FIGS. 15$a$ and 15$b$). The colistin-dependent capture of two independently isolated *A. baumannii* strains that are strongly colistin resistant implies a previously unrecognized approach for the capture and removal of antibiotic-resistant bacteria (FIGS. 15$c$ and 5$d$). This result is consistent with colistin-resistance as independent of colistin binding to the bacterial outer membrane. These colistin-resistant strains have increased expression of many genes involved in cell envelope and membrane biogenesis. The inability of colistin functionalized double spiral devices to capture Gram-positive bacteria, such as *B. subtilis* 1A578, further supports the capture mechanism as colistin recognition since Gram-positive bacteria are insensitive to, and unable to bind, colistin. Endotoxin, a Gram-negative bacterial toxin that can elicit sepsis-related complications, was removed from fluid with nearly 100% capture efficiency upon flow through the colistin-functionalized device (FIG. 23).

Figure 16:
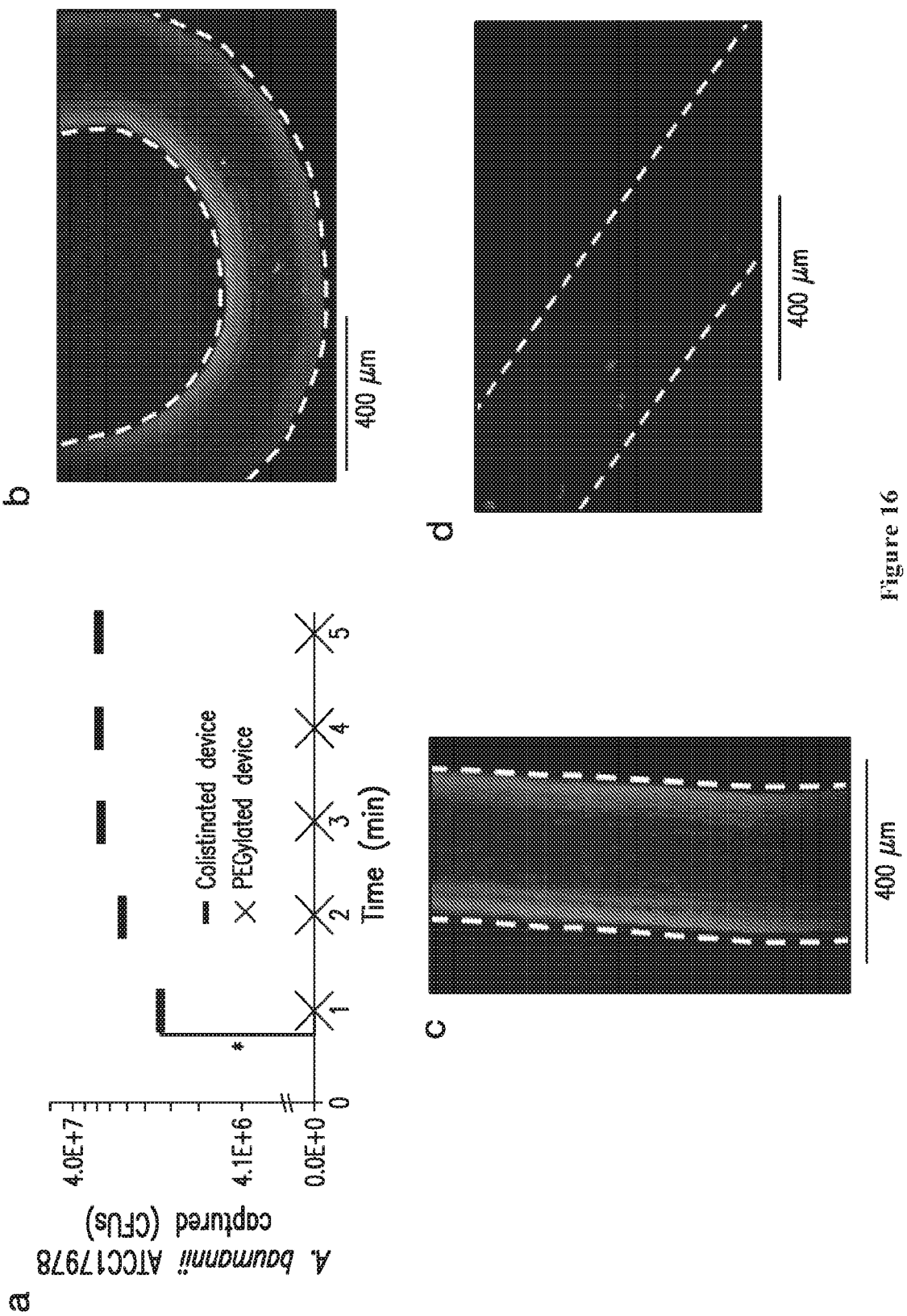
FIG. 16 shows the ex vivo blood cleansing using a double spiral configuration of the claimed fluidic device. a, Capture capacity for *A. baumannii* ATCC17978 when spiked into whole, human blood and flowed through the colistinated and PEGylated device at 0.2 ml min$^{-1}$. Results are plotted as the mean±SD, n=3. *P<0.01. b & c, Green fluorescently labeled.

Robust bacterial capture from blood is essentially identical to that for blood cell-free bacterial suspensions in vitro (FIGS. 16 and 17). The design of the double spiral spatially isolates the formed elements of the blood from the regions where bacterial binding occurs and is hypothesized to be responsible for bacterial capture efficiency that is not reduced in the presence of blood cells. Septic humans are estimated to contain a maximum of $10^3$ CFUs of bacteria in the blood at any particular time during the infection. The demonstrated capacity of this design exceeds the average number of bacteria in the blood of a septic human by more than three orders of magnitude. Therefore, considerable capture capacity exists in this device to accommodate additional bacteria that enter the blood compartment from the source of infection, such as the lungs. The simplicity and robustness of this design supports the translational potential of the approach.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A fluidic device for capture or removal of disease-causing material from a biological fluid comprising:
   a multidirectional channel between one inlet and up to five outlets, said channel comprising an inner wall; and
   a disease material-targeting ligand functionalized on at least a portion of the inner wall of the channel;
   wherein the functionalized disease material-targeting ligand is effective in capturing pathogens or endotoxins from the biological fluid to allow the biological fluid to emerge from the device substantially free of the disease-causing material and suitable for return to a subject, and wherein the functionalized disease material-targeting ligand is an antibiotic.

2. The device of claim 1, wherein the multidirectional channel comprises a spiral.

3. The device of claim 1, wherein the multidirectional channel comprises a double spiral.

4. The device of claim 1, wherein the functionalized disease material-targeting ligand comprises:
a Gram-positive ligand; or
a Gram-negative ligand.

5. The device of claim 1, wherein the antibiotic comprises:
colistin;
vancomycin; or
a combination thereof.

6. The device of claim 1, wherein the channel is composed of at least one thermoplastic polymer base material that has at least one surface exposed functional group selected from the groups consisting of: carbonyl groups, carboxyl groups, alcohol groups, amino groups, chloride groups, styrene groups, alpha-halogenated acyl group, benzyl groups, isocyanic acid groups, and other polymers or copolymers such as acrylamide, polydimethylsiloxane, polyethylene, acrylonitrile, maleic anhydride and polymethyl methacrylate.

7. The device of claim 6, wherein the channel base material is polycarbonate.

8. The device of claim 1, wherein the channel has a width to height aspect ratio equal to or greater than 1:1, but no more than 50:1.

9. The device of claim 8, wherein the channel has a width and height between the range of about 0.01 cm to about 30 cm.

10. The device of claim 1, wherein the channel has a length between about 0.0005 cm and about 1,000.0 cm.

11. The device of claim 1, wherein the channel comprises four or more loops.

12. The device of claim 11, wherein an outermost radius of the four or more loops of the channel is about 9.8 mm or greater.

13. The device of claim 1, wherein a spacing between two adjacent loops of the channel is about 500 μm.

14. The device of claim 1, wherein the channel is present in only one plane.

15. The device of claim 1, wherein a height of the device can have a range between about 15 μm and about 100 cm.

16. The device of claim 1, wherein a height of the device can have a range between about 15 μm and about 500 cm.

17. The device of claim 1, wherein the channel is three-dimensionally shaped as a helix.

* * * * *